(12) United States Patent
Kurose et al.

(10) Patent No.: US 9,724,312 B2
(45) Date of Patent: Aug. 8, 2017

(54) AGENT FOR THE PREVENTION, IMPROVEMENT OR TREATMENT OF RETINAL DISEASE

(71) Applicant: ROHTO PHARMACEUTICAL CO., LTD., Osaka (JP)

(72) Inventors: Takahiro Kurose, Osaka (JP); Takayuki Miyano, Osaka (JP); Mariyo Kato, Osaka (JP); Yoshihiro Takai, Osaka (JP)

(73) Assignee: ROHTO PHARMACEUTICAL CO., LTD., Osaka (JP)

( * ) Notice: Subject to any disclaimer, the term of this patent is extended or adjusted under 35 U.S.C. 154(b) by 0 days.

(21) Appl. No.: 14/154,688

(22) Filed: Jan. 14, 2014

(65) Prior Publication Data

US 2014/0128475 A1    May 8, 2014

Related U.S. Application Data

(63) Continuation of application No. 13/775,605, filed on Feb. 25, 2013, now abandoned.

(60) Provisional application No. 61/638,724, filed on Apr. 26, 2012.

(30) Foreign Application Priority Data

Feb. 27, 2012   (JP) ................. 2012-040803

(51) Int. Cl.
| | | |
|---|---|---|
| A61K 31/121 | (2006.01) | |
| A61K 47/02 | (2006.01) | |
| A61K 45/06 | (2006.01) | |
| A61K 9/00 | (2006.01) | |
| A61K 47/26 | (2006.01) | |
| A61K 47/44 | (2017.01) | |

(52) U.S. Cl.
CPC .......... *A61K 31/121* (2013.01); *A61K 9/0048* (2013.01); *A61K 9/0053* (2013.01); *A61K 45/06* (2013.01); *A61K 47/02* (2013.01); *A61K 47/26* (2013.01); *A61K 47/44* (2013.01)

(58) Field of Classification Search
CPC .................................................... A61K 31/121
See application file for complete search history.

(56) References Cited

U.S. PATENT DOCUMENTS

| | | | |
|---|---|---|---|
| 2005/0009772 A1* | 1/2005 | Caprioli | ............... 514/44 |
| 2010/0004156 A1 | 1/2010 | Kaushal et al. | |
| 2012/0172453 A1 | 7/2012 | Barres et al. | |

FOREIGN PATENT DOCUMENTS

| | | |
|---|---|---|
| JP | 6-192073 | 7/1994 |
| JP | 8-133967 | 5/1996 |
| JP | 2000-319170 | 11/2000 |
| JP | 3560072 | 6/2004 |
| JP | 2009-507770 | 2/2009 |
| WO | 2012/031028 | 3/2012 |
| WO | 2013/129315 | 9/2013 |

OTHER PUBLICATIONS

M. Kayama et al., "Heat Shock Protein 70 (HSP70) Is Critical for the Photoreceptor Stress Response after Retinal Detachment Via Modulating Anti-Apoptotic Akt Kinase", The American Journal of Pathology, vol. 178, No. 3, Mar. 2011, pp. 1080-1091.
Y. Ishii et al., "Retinal Ganglion Cell Protection With Geranylgeranylacetone, a Heat Shock Protein Inducer, in a Rat Glaucoma Model", Investigative Ophthalmology & Visual Science, May 2003, vol. 44, No. 5, pp. 1982-1992.
M. Tanito et al., "Cytoprotective Effects of Geranylgeranylacetone against Retinal Photooxidative Damage", The Journal of Neuroscience, Mar. 2, 2005, vol. 25, No. 9, pp. 2396-2404.
C. Harada et al., "Neuroprotective effect of geranylgeranylacetone against ischemia-induced retinal injury", Molecular Vision, vol. 13, 2007, pp. 1601-1607.
X. Guo et al., "Effect of geranylgeranylacetone on optic neuritis in experimental autoimmune encephalomyelitis", Neuroscience Letters, vol. 462, 2009, pp. 281-285.
M. Murakami et al., "Effect of synthetic acyclic polyisoprenoids on the cold-restraint stress induced gastric ulcer in rats", Japan. J. Pharmacol., vol. 33, 1983, pp. 549-556.
International Search Report issued Apr. 9, 2013 in International Application No. PCT/JP2013/054774.
International Preliminary Report on Patentability issued Sep. 12, 2014 in International Application No. PCT/JP2013/054774.

\* cited by examiner

*Primary Examiner* — Zohreh Fay
(74) *Attorney, Agent, or Firm* — Wenderoth, Lind & Ponack, L.L.P.

(57) ABSTRACT

A prophylactic, ameliorating or therapeutic agent for a retinal disease, the agent comprising geranylgeranylacetone which (a) is a mixture of (5E,9E,13E)-geranylgeranylacetone and (5Z,9E,13E)-geranylgeranylacetone, the (5E,9E,13E)-geranylgeranylacetone content of the mixture being 80% by weight or more,
(b) consists of (5E,9E,13E)-geranylgeranylacetone, or
(c) consists of (5Z,9E,13E)-geranylgeranylacetone directly suppresses the death of a retinal cell, thereby fundamentally preventing, ameliorating or treating the retinal disease.

13 Claims, 5 Drawing Sheets
(1 of 5 Drawing Sheet(s) Filed in Color)

※The weight ratio of the all-trans form:the 5Z-mono-cis form

※The weight ratio of the all-trans form:the 5Z-mono-cis form

※The weight ratio of the all-trans form:the 5Z-mono-cis form

AGENT FOR THE PREVENTION, IMPROVEMENT OR TREATMENT OF RETINAL DISEASE

TECHNICAL FIELD

The present invention relates to a prophylactic, ameliorating or therapeutic agent for a retinal disease.

BACKGROUND ART

Teprenone (Eisai Co., Ltd.) is a mixture of (5E,9E,13E)-geranylgeranylacetone and (5Z,9E,13E)-geranylgeranylacetone at a weight ratio of 3:2. Teprenone is widely used as an oral therapeutic agent for gastric ulcer.

The use of teprenone in the ophthalmic field has been suggested. For example, Patent Literature 1 teaches the use of teprenone as an active ingredient of a prophylactic or therapeutic agent for dry eye, eye strain, or eye dryness. Patent Literature 2 discloses a clear eye drop consisting of teprenone, a phospholipid, a synthetic surfactant, and water.

Geranylgeranylacetone with an unknown cis-trans isomer ratio (Eisai Co., Ltd.) is also known to be useful as an active ingredient of a therapeutic agent for a retinal disease.

For example, Patent Literature 3 teaches a method for ameliorating an ocular disease such as diabetic retinopathy and glaucoma in a patient, the method comprising administering geranylgeranylacetone to the patient to increase the expression or activity of a heat shock protein in an ocular tissue, and recruiting a stem cell to the ocular tissue, thereby ameliorating the ocular disease.

Non Patent Literature 1 teaches that intraperitoneal administration of geranylgeranylacetone to a retinal detachment-induced animal induced the expression of heat shock protein 70 and subsequently reduced the apoptosis of visual cells significantly.

Non Patent Literature 2 teaches that intraperitoneal administration of geranylgeranylacetone to a glaucoma rat model induced the expression of heat shock protein 72 and subsequently reduced retinal ganglion cell death and thereby ameliorated optic nerve damage.

Non Patent Literature 3 teaches that oral administration of geranylgeranylacetone to a mouse with visual cell damage induced by light irradiation induced thioredoxin and heat shock protein 72 in the retinal pigment epithelium. The literature also teaches that the release of thioredoxin from the retinal pigment epithelium plays a crucial role in maintaining visual cells and that geranylgeranylacetone is useful for the protection of visual cells against light damage.

Non Patent Literature 4 teaches that oral administration of geranylgeranylacetone to a mouse with retinal injury induced by ischemia significantly increased the number of surviving retinal neurons and that geranylgeranylacetone is useful for the treatment of retinal degenerative diseases that involve ischemic injury.

Non Patent Literature 5 teaches that oral administration of geranylgeranylacetone to a multiple sclerosis mouse model improved the visual function, reduced the number of degenerating axons in the optic nerve, and prevented cell loss in the ganglion.

Teprenone marketed by Eisai Co., Ltd. is a mixture of (5E,9E,13E)-geranylgeranylacetone and (5Z,9E,13E)-geranylgeranylacetone at a weight ratio of 3:2 (WO 2004/047822, JP-9-169639 A, JP Pat. No. 4621326, JP-2006-89393 A, the Japanese pharmacopoeia, 16th edition, and the package insert of Selbex). Hence geranylgeranylacetone described in Patent Literature 3 and Non Patent Literature 1 to 5 is also a mixture of (5E,9E,13E)-geranylgeranylacetone and (5Z,9E,13E)-geranylgeranylacetone at a weight ratio of 3:2. Teprenone marketed by companies other than Eisai Co., Ltd. are also mixtures of (5E,9E,13E)-geranylgeranylacetone and (5Z,9E,13E)-geranylgeranylacetone at a weight ratio of 3:2 (for example, see MSDS (Cat. No. 202-15733; Wako Pure Chemical Industries, Ltd.).

However, teprenone, which is a mixture of (5E,9E,13E)-geranylgeranylacetone and (5Z,9E,13E)-geranylgeranylacetone at a weight ratio of 3:2, lacks a practically sufficient ameliorating effect for a retinal disease.

CITATION LIST

Patent Literature

Patent Literature 1: JP-8-133967 A
Patent Literature 2: JP-2000-319170 A
Patent Literature 3: JP-2009-507770 A

Non Patent Literature

Non Patent Literature 1: The American Journal of Pathology, Vol. 178, No. 3, March 2011, 1080-1090
Non Patent Literature 2: Investigative Ophthalmology & Visual Science, May 2003, Vol. 44, No. 5, 1982-1992
Non Patent Literature 3: The Journal of Neuroscience, Mar. 2, 2005, 25(9), 2396-2404
Non Patent Literature 4: Molecular vision, 2007, 13, 1601-1607
Non Patent Literature 5: Neuroscience Letters, 462, 2009, 281-285

SUMMARY OF INVENTION

Technical Problem

An object of the present invention is to provide a prophylactic, ameliorating or therapeutic agent having a practically sufficient effect for a retinal disease.

Solution to Problem

The inventors conducted extensive research in order to solve the above problem and found the following unexpected findings.

(i) Geranylgeranylacetone has a protective action for a retinal cell and is very effective in the prevention, amelioration and treatment of a retinal disease. The effect is high when (5E,9E,13E)-geranylgeranylacetone (hereinafter sometimes referred to as "all-trans form") or (5Z,9E,13E)-geranylgeranylacetone (hereinafter sometimes referred to as "5Z-mono-cis form") is used, whereas the effect is low when a mixture thereof is used.

(ii) The all-trans form has a far superior protective effect for a retinal cell to teprenone, which is a mixture of the all-trans form and the 5Z-mono-cis form at a weight ratio of 3:2.

(iii) When the all-trans form content of a mixture of the all-trans form and the 5Z-mono-cis form is 80% by weight or more, the protective effect for a retinal cell is significantly high.

(iv) When the 5Z-mono-cis form content of a mixture of the all-trans form and the 5Z-mono-cis form is very high, the protective effect for a retinal cell is also significantly high.

The present invention has been completed based on the above findings and provides a prophylactic, ameliorating or therapeutic agent for a retinal disease, as described below.

(1) A prophylactic, ameliorating or therapeutic agent for a retinal disease, the agent comprising geranylgeranylacetone which
(a) is a mixture of (5E,9E,13E)-geranylgeranylacetone and (5Z,9E,13E)-geranylgeranylacetone, the (5E,9E,13E)-geranylgeranylacetone content of the mixture being 80% by weight or more,
(b) consists of (5E,9E,13E)-geranylgeranylacetone, or
(c) consists of (5Z,9E,13E)-geranylgeranylacetone.

(2) The agent according to the above (1), which is an ophthalmic preparation.

(3) The agent according to the above (2), wherein the geranylgeranylacetone content is 0.00001 to 10% by weight relative to the total amount of the preparation.

(4) The agent according to the above (1), which is an oral agent.

(5) The agent according to the above (4), wherein the geranylgeranylacetone content is 0.001 to 80% by weight relative to the total amount of the preparation.

(6) The agent according to any of the above (1) to (5), wherein the retinal disease is a disease selected from the group consisting of glaucoma, retinitis pigmentosa, age-related macular degeneration and diabetic retinopathy.

(7) The agent according to any of the above (1) to (6), whose pH is from 6 to 8.

(8) The agent according to any of the above (1) to (7), which further comprises a phosphate buffering agent.

(9) A protective agent for a retinal cell, the agent comprising as an active ingredient geranylgeranylacetone which
(a) is a mixture of (5E,9E,13E)-geranylgeranylacetone and (5Z,9E,13E)-geranylgeranylacetone, the (5E,9E,13E)-geranylgeranylacetone content of the mixture being 80% by weight or more,
(b) consists of (5E,9E,13E)-geranylgeranylacetone, or
(c) consists of (5Z,9E,13E)-geranylgeranylacetone.

(10) The agent according to the above (9), which is an ophthalmic preparation.

(11) The agent according to the above (10), wherein the geranylgeranylacetone content is 0.00001 to 10% by weight relative to the total amount of the preparation.

(12) The agent according to the above (9), which is an oral agent.

(13) The agent according to the above (12), wherein the geranylgeranylacetone content is 0.001 to 80% by weight relative to the total amount of the preparation.

(14) The agent according to any of the above (9) to (13), wherein the retinal cell is a retinal ganglion cell or a retinal pigment epithelial cell.

(15) The agent according to any of the above (9) to (14), whose pH is from 6 to 8.

(16) The agent according to any of the above (9) to (13), which further comprises a phosphate buffering agent.

(17) A suppressing agent for the degeneration, impairment or destruction of a retinal cell, the agent comprising as an active ingredient geranylgeranylacetone which
(a) is a mixture of (5E,9E,13E)-geranylgeranylacetone and (5Z,9E,13E)-geranylgeranylacetone, the (5E,9E,13E)-geranylgeranylacetone content of the mixture being 80% by weight or more,
(b) consists of (5E,9E,13E)-geranylgeranylacetone, or
(c) consists of (5Z,9E,13E)-geranylgeranylacetone.

(18) The agent according to the above (17), which is an ophthalmic preparation.

(19) The agent according to the above (18), wherein the geranylgeranylacetone content is 0.00001 to 10% by weight relative to the total amount of the preparation.

(20) The agent according to the above (17), which is an oral agent.

(21) The agent according to the above (20), wherein the geranylgeranylacetone content is 0.001 to 80% by weight relative to the total amount of the preparation.

(22) The agent according to any of the above (17) to (21), wherein the retinal cell is a retinal ganglion cell or a retinal pigment epithelial cell.

(23) The agent according to any of the above (17) to (22), whose pH is from 6 to 8.

(24) The agent according to any of the above (17) to (23), which further comprises a phosphate buffering agent.

(25) A composition for use in the prevention, amelioration or treatment of a retinal disease, the composition comprising geranylgeranylacetone which
(a) is a mixture of (5E,9E,13E)-geranylgeranylacetone and (5Z,9E,13E)-geranylgeranylacetone, the (5E,9E,13E)-geranylgeranylacetone content of the mixture being 80% by weight or more,
(b) consists of (5E,9E,13E)-geranylgeranylacetone, or
(c) consists of (5Z,9E,13E)-geranylgeranylacetone.

(26) Use of geranylgeranylacetone for the production of a prophylactic, ameliorating or therapeutic agent for a retinal disease, the geranylgeranylacetone
(a) being a mixture of (5E,9E,13E)-geranylgeranylacetone and (5Z,9E,13E)-geranylgeranylacetone, the (5E,9E, 13E)-geranylgeranylacetone content of the mixture being 80% by weight or more,
(b) consisting of (5E,9E,13E)-geranylgeranylacetone, or
(c) consisting of (5Z,9E,13E)-geranylgeranylacetone.

(27) Use of geranylgeranylacetone as a prophylactic, ameliorating or therapeutic agent for a retinal disease, the geranylgeranylacetone
(a) being a mixture of (5E,9E,13E)-geranylgeranylacetone and (5Z,9E,13E)-geranylgeranylacetone, the (5E,9E, 13E)-geranylgeranylacetone content of the mixture being 80% by weight or more,
(b) consisting of (5E,9E,13E)-geranylgeranylacetone, or
(c) consisting of (5Z,9E,13E)-geranylgeranylacetone.

(28) A method for preventing, ameliorating or treating a retinal disease, the method comprising the step of administering to a patient with a retinal disease an effective amount of geranylgeranylacetone which
(a) is a mixture of (5E,9E,13E)-geranylgeranylacetone and (5Z,9E,13E)-geranylgeranylacetone, the (5E,9E,13E)-geranylgeranylacetone content of the mixture being 80% by weight or more, or
(b) consists of (5E,9E,13E)-geranylgeranylacetone, thereby preventing, ameliorating or treating the retinal disease.

(29) A composition for use in the protection of a retinal cell, the composition comprising geranylgeranylacetone which
(a) is a mixture of (5E,9E,13E)-geranylgeranylacetone and (5Z,9E,13E)-geranylgeranylacetone, the (5E,9E,13E)-geranylgeranylacetone content of the mixture being 80% by weight or more,
(b) consists of (5E,9E,13E)-geranylgeranylacetone, or
(c) consists of (5Z,9E,13E)-geranylgeranylacetone.

(31) Use of geranylgeranylacetone as a protective agent for a retinal cell, the geranylgeranylacetone
(a) being a mixture of (5E,9E,13E)-geranylgeranylacetone and (5Z,9E,13E)-geranylgeranylacetone, the (5E,9E, 13E)-geranylgeranylacetone content of the mixture being 80% by weight or more, (b) consisting of (5E,9E,13E)-geranylgeranylacetone, or
(c) consisting of (5Z,9E,13E)-geranylgeranylacetone.

(30) Use of geranylgeranylacetone for the production of a protective agent for a retinal cell, the geranylgeranylacetone
(a) being a mixture of (5E,9E,13E)-geranylgeranylacetone and (5Z,9E,13E)-geranylgeranylacetone, the (5E,9E,13E)-geranylgeranylacetone content of the mixture being 80% by weight or more,
(b) consisting of (5E,9E,13E)-geranylgeranylacetone, or
(c) consisting of (5Z,9E,13E)-geranylgeranylacetone.

(32) A method for protecting a retinal cell, the method comprising the step of administering to a patient with a retinal disease an effective amount of geranylgeranylacetone which
(a) is a mixture of (5E,9E,13E)-geranylgeranylacetone and (5Z,9E,13E)-geranylgeranylacetone, the (5E,9E,13E)-geranylgeranylacetone content of the mixture being 80% by weight or more,
(b) consists of (5E,9E,13E)-geranylgeranylacetone, or
(c) consists of (5Z,9E,13E)-geranylgeranylacetone, thereby protecting a retinal cell.

(33) A composition for use in the suppression of the degeneration, impairment or destruction of a retinal cell, the composition comprising geranylgeranylacetone which
(a) is a mixture of (5E,9E,13E)-geranylgeranylacetone and (5Z,9E,13E)-geranylgeranylacetone, the (5E,9E,13E)-geranylgeranylacetone content of the mixture being 80% by weight or more,
(b) consists of (5E,9E,13E)-geranylgeranylacetone, or
(c) consists of (5Z,9E,13E)-geranylgeranylacetone.

(34) Use of geranylgeranylacetone for the production of a suppressing agent for the degeneration, impairment or destruction of a retinal cell, the geranylgeranylacetone
(a) being a mixture of (5E,9E,13E)-geranylgeranylacetone and (5Z,9E,13E)-geranylgeranylacetone, the (5E,9E,13E)-geranylgeranylacetone content of the mixture being 80% by weight or more,
(b) consisting of (5E,9E,13E)-geranylgeranylacetone, or
(c) consisting of (5Z,9E,13E)-geranylgeranylacetone.

(35) Use of geranylgeranylacetone as a suppressing agent for the degeneration, impairment or destruction of a retinal cell, the geranylgeranylacetone
(a) being a mixture of (5E,9E,13E)-geranylgeranylacetone and (5Z,9E,13E)-geranylgeranylacetone, the (5E,9E,13E)-geranylgeranylacetone content of the mixture being 80% by weight or more,
(b) consisting of (5E,9E,13E)-geranylgeranylacetone, or
(c) consisting of (5Z,9E,13E)-geranylgeranylacetone.

(36) A method for suppressing the degeneration, impairment or destruction of a retinal cell, the method comprising the step of administering to a patient with a retinal disease an effective amount of geranylgeranylacetone which
(a) is a mixture of (5E,9E,13E)-geranylgeranylacetone and (5Z,9E,13E)-geranylgeranylacetone, the (5E,9E,13E)-geranylgeranylacetone content of the mixture being 80% by weight or more,
(b) consists of (5E,9E,13E)-geranylgeranylacetone, or
(c) consists of (5Z,9E,13E)-geranylgeranylacetone, thereby suppressing the degeneration, impairment or destruction of a retinal cell.

Advantageous Effects of Invention

The agent of the present invention comprising geranylgeranylacetone (hereinafter sometimes abbreviated to "GGA") having the all-trans form content of 80% by weight or more protects various types of retinal cells from degeneration, impairment or destruction, thereby remarkably promoting the survival. Consequently, the agent exhibits a remarkable effect of preventing, ameliorating or treating various retinal diseases.

GGA having the all-trans form content of 80% by weight or more can exhibit the protective action for a retinal cell even in a small amount, and the agent of the present invention is therefore not required to comprise a high level of GGA. In contrast, generally the components of an ophthalmic preparation have poor penetration into the eyeball and are hence used at a relatively high concentration. Therefore, the fact that the agent of the present invention requires only a low level of GGA is a great advantage as an ophthalmic preparation.

Conventional therapeutic agents for retinal diseases indirectly protect retinal cells through, for example, reduction in the intraocular pressure, thereby suppressing retinal neuronal cell death due to the elevation of intraocular pressure. In contrast, the agent of the present invention directly suppresses retinal cell death and thus fundamentally prevents, ameliorates or treats a retinal disease. Therefore, the agent of the present invention is very useful as a therapeutic agent for a retinal disease.

In addition, since GGA has been widely used and the safety has been established, the agent of the present invention is safe.

Further, the agent of the present invention can be formulated into a dosage form that the patient can easily take at home, for example, an eye drop or an oral agent and is therefore useful as a prophylactic, ameliorating or therapeutic agent for a serious retinal disease.

A liquid preparation comprising teprenone, which is a mixture of the all-trans form and the 5Z-mono-cis form at a weight ratio of 3:2, tends to become white turbid when stored at low temperature. Consequently, during commercial distribution to or during storage in cold areas, such a liquid preparation becomes white turbid, which reduces its commercial value.

In this regard, the agent of the present invention comprising GGA having the all-trans form content of 80% by weight or more hardly becomes white turbid even when stored at low temperature. Therefore, the agent of the present invention can be commercially distributed to any area and thus its commercial value is high.

Further, an ophthalmic composition of the present invention comprising GGA having the all-trans form content of 80% by weight or more exhibits reduced eye irritancy.

Mono-cis-GGA and GGA that is a mixture of the all-trans form and the mono-cis form and has a very high mono-cis form content also have a protective action for a retinal cell and are very effective in the prevention, amelioration and treatment of a retinal disease. Their effects are far superior to that of teprenone, which is a mixture of the all-trans form and the 5Z-mono-cis form at a weight ratio of 3:2.

BRIEF DESCRIPTION OF DRAWINGS

The patent or application file contains at least one drawings executed in color. Copies of this patent or patent application with color drawing(s) will be provided by the Office upon request and payment of the necessary fee.

DESCRIPTION OF EMBODIMENTS

Figure 1:
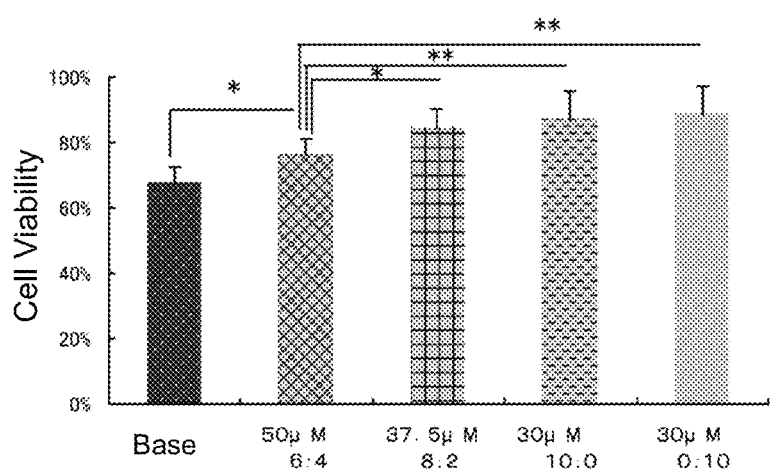
FIG. 1 shows the cytoprotective effect of GGA against ischemic cell death induced by hypoxia and low glucose.

The present invention will be described in detail below.

A prophylactic, ameliorating or therapeutic agent for a retinal disease of the present invention comprises GGA as an active ingredient.

GGA herein is entirely in the all-trans form; entirely in the mono-cis form; a mixture of the all-trans form and the mono-cis form, the mixture having the all-trans form content of 80% by weight or more; or a mixture of the all-trans form and the mono-cis form, the mixture having a very high mono-cis form content.

Geranylgeranylacetone (1) Types of Geometric Isomers

GGA has eight geometric isomers. Specifically, the eight geometric isomers are:
(5E,9E,13E)-6,10,14,18-tetramethyl-5,9,13,17-nonadecatetraen-2-one (5E,9E,13E GGA) (all-trans form),
(5Z,9E,13E)-6,10,14,18-tetramethyl-5,9,13,17-nonadecatetraen-2-one (5Z,9E,13E GGA) (5Z-mono-cis form),
(5Z,9Z,13E)-6,10,14,18-tetramethyl-5,9,13,17-nonadecatetraen-2-one (5Z,9Z,13E GGA) (13E-mono-trans form),
(5Z,9Z,13Z)-6,10,14,18-tetramethyl-5,9,13,17-nonadecatetraen-2-one (5Z,9Z,13Z GGA) (all-cis form),
(5E,9Z,13E)-6,10,14,18-tetramethyl-5,9,13,17-nonadecatetraen-2-one (5E,9Z,13E GGA) (9Z-mono-cis form),
(5E,9Z,13Z)-6,10,14,18-tetramethyl-5,9,13,17-nonadecatetraen-2-one (5E,9Z,13Z GGA) (5E-mono-trans form),
(5E,9E,13Z)-6,10,14,18-tetramethyl-5,9,13,17-nonadecatetraen-2-one (5E,9E,13Z GGA) (13Z-mono-cis form), and
(5Z,9E,13Z)-6,10,14,18-tetramethyl-5,9,13,17-nonadecatetraen-2-one (5Z,9E,13Z GGA) (9E-mono-trans form).

In the present invention, GGA consists of the all-trans form, consists of the mono-cis form, or is a mixture of the all-trans form and the mono-cis form. The mono-cis form may be any of the 5Z-mono-cis form, the 9Z-mono-cis form, and the 13Z-mono-cis form, or a combination of two or more thereof.

Preferably the mono-cis form is the 5Z-mono-cis form.

In cases where GGA is a mixture of the all-trans form and the mono-cis form (in particular the 5Z-mono-cis form), the all-trans form content of the mixture is 80% by weight or more, preferably 82% by weight or more, more preferably 84% by weight or more, further more preferably 86% by weight or more, further more preferably 88% by weight or more, further more preferably 90% by weight or more, further more preferably 92% by weight or more, further more preferably 94% by weight or more, further more preferably 96% by weight, further more preferably 98% by weight or more. Especially preferably, GGA consists of the all-trans form. The mixture having the all-trans form content in the above ranges exhibits a remarkable effect of preventing, ameliorating or treating a retinal disease and hardly becomes white turbid when stored at low temperature.

A mixture of the all-trans form and the mono-cis form (in particular the 5Z-mono-cis form) with a very high mono-cis form (in particular the 5Z-mono-cis form) ratio is also preferred due to its remarkable prophylactic, ameliorating or therapeutic effect for a retinal disease.

(2) All-Trans Form and 5Z-Mono-Cis Form (5E,9E,13E)-geranylgeranylacetone (the all-trans form) is a compound represented by the following structural formula:

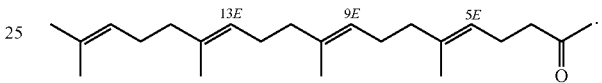

The all-trans form can be purchased from, for example, Rionlon Development Co., Ltd.

The all-trans form can also be obtained through separating the all-trans form and the 5Z-mono-cis form of a marketed teprenone (Eisai Co., Ltd., Wako Pure Chemical Industries, Ltd., Yoshindo Inc., etc.) by, for example, silica gel chromatography using a mobile phase of n-hexane/ethyl acetate (9:1). The separation of the all-trans form and the 5Z-mono-cis form of a marketed teprenone can also be commissioned to, for example, KNC Laboratories Co., Ltd.

(5Z,9E,13E)-geranylgeranylacetone (the 5Z-mono-cis form) can also be obtained by the separation from a marketed teprenone. The 5Z-mono-cis form is a compound represented by the following structural formula:

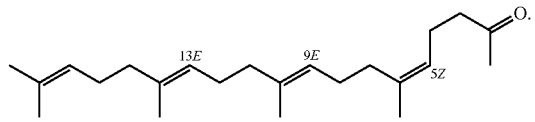 [SMILES: CC(=O)CC/C=C(/C)CC/C=C(\C)CC/C=C(\C)CCC=C(C)C]

The all-trans form can also be synthesized in accordance with a method described in, for example, Bull. Korean Chem. Soc., 2009, Vol. 30, No. 9, 215-217. This literature describes, for example, the method shown by the following synthesis scheme:

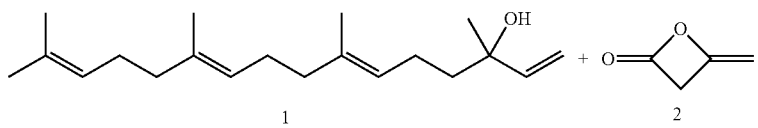

-continued

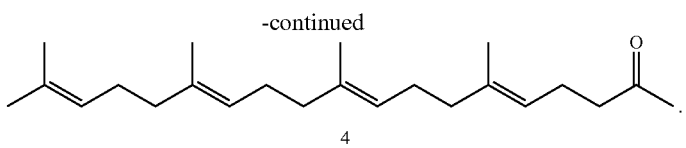

4

Specifically, in the above reaction formula, geranyllinalool 1 is mixed with Compound 2 and aluminum isopropoxide, and the mixture is gradually heated to 130° C. to allow the reaction to occur. After the completion of the reaction, the residue Compound 2 is removed and the reaction mixture is diluted with 5% sodium carbonate so that the residue aluminum propoxide is quenched. In this way, the all-trans form can be obtained. The obtained all-trans form is subsequently purified by, for example, silica gel chromatography using dichloromethane as an eluent.

(3) Mixtures of all-Trans Form and 5Z-Mono-Cis Form

Mixtures of the all-trans form and the 5Z-mono-cis form can be obtained by adding the all-trans form or the 5Z-mono-cis form to a marketed teprenone.

Preparations

The dosage form of the agent of the present invention is not particularly limited and any known pharmaceutical dosage form can be employed without limitation. Examples thereof include an ophthalmic agent, an oral agent, an injection (an intravenous injection, a hypodermic injection, an intramuscular injection, etc.), a percutaneous absorption agent, a suppository, and inhalant. Among these, preferred are an ophthalmic agent, an oral agent, or a percutaneous absorption agent and more preferred is an ophthalmic agent in terms of the effectiveness as a prophylactic, ameliorating or therapeutic agent for a retinal disease and the easiness of use for the patient.

The preparation in any of these dosage forms can comprise, in addition to GGA, a pharmaceutically acceptable base or carrier, a pharmaceutically acceptable additive, and/or a physiologically or pharmacologically active component other than GGA.

(1) Ophthalmic Agent

The form of an ophthalmic agent is not particularly limited and may be in any form such as a liquid, a fluid, a gel, a semi-solid, and a solid.

The type of the ophthalmic agent is not particularly limited. Examples thereof include an eye drop, an eye wash, a contact lens-wearing solution, a contact lens solution (e.g., a washing solution, a storage solution, a sterilizing solution, a multipurpose solution, a package solution, etc.), a preservative for a harvested ocular tissue (a cornea etc.) for transplantation, an irrigating solution for surgery, an ophthalmic ointment (e.g., a water-soluble ophthalmic ointment, an oil-soluble ophthalmic ointment, etc.), an intraocular injection (e.g., an intravitreal injection), etc.

The ophthalmic agent in the form other than a solid, for example, a liquid, a fluid, a gel, or a semi-solid or the ophthalmic agent in a solid form may be an aqueous composition or an oil composition such as an ointment.

Preparation methods for an ophthalmic preparation are well known. An ophthalmic preparation can be prepared by mixing GGA with a pharmaceutically acceptable base or carrier, and as needed a pharmaceutically acceptable additive for an ophthalmic preparation and another active ingredient (a physiologically or pharmacologically active component).

<Bases or Carriers>

Examples of the base or carrier include water; an aqueous solvent such as a polar solvent; a polyalcohol; a vegetable oil; and an oily base. Examples of the base or carrier for an intraocular injection include water for injection and physiological saline.

These bases or carriers can be used alone or in combination of two or more thereof.

<Additives>

Examples of the additive include a surfactant, a flavor or cooling agent, an antiseptic, a bactericide or antibacterial agent, a pH adjusting agent, a tonicity agent, a chelating agent, a buffering agent, a stabilizer, an antioxidant, and a thickening agent. An intraocular injection may contain a solubilizing agent, a suspending agent, a tonicity agent, a buffering agent, a soothing agent, a stabilizer, and an antiseptic.

These additives can be used alone or in combination of two or more thereof.

The additives will be exemplified below.

Surfactants: for example, nonionic surfactants such as polyoxyethylene (hereinafter sometimes referred to as "POE")-polyoxypropylene (hereinafter sometimes referred to as "POP") block copolymers (e.g., poloxamer 407, poloxamer 235, poloxamer 188), ethylenediamine POE-POP block copolymer adducts (e.g., poloxamine), POE sorbitan fatty acid esters (e.g., polysorbate 20, polysorbate 60, polysorbate 80 (TO-10 etc.)), POE hydrogenated castor oils (e.g., POE (60) hydrogenated castor oil (HCO-60 etc.)), POE castor oils, POE alkyl ethers (e.g., polyoxyethylene (9) lauryl ether, polyoxyethylene (20) polyoxypropylene (4) cetyl ether), and polyoxyl stearate;
amphoteric surfactants such as glycine-type amphoteric surfactants (e.g., alkyl diaminoethyl glycine, alkyl polyaminoethyl glycine), betaine-type amphoteric surfactants (e.g., lauryldimethylaminoacetic betaine, imidazolinium betaine); cationic surfactants such as alkyl quaternary ammonium salts (e.g., benzalkonium chloride, benzethonium chloride); etc.

The numbers in the parentheses represent the molar number of added POE or POP.

Flavors or cooling agents: for example, camphor, borneol, terpenes (these may be in the d-form, l-form, or dl-form); essential oils such as mentha water, eucalyptus oil, bergamot oil, anethole, eugenol, geraniol, menthol, limonene, mentha oil, peppermint oil, rose oil, etc.

Antiseptics, bactericides, or antibacterial agents: for example, polidronium chloride, alkyldiaminoethylglycine hydrochloride, sodium benzoate, ethanol, benzalkonium chloride, benzethonium chloride, chlorhexidine gluconate, chlorobutanol, sorbic acid, potassium sorbate, sodium dehydroacetate, methyl paraoxybenzoate, ethyl paraoxybenzoate, propyl paraoxybenzoate, butyl paraoxybenzoate, oxyquinoline sulfate, phenethyl alcohol, benzyl alcohol, biguanide compounds (in particular, polyhexamethylene biguanide or its hydrochloride etc.), Glokill (Rhodia Ltd.), etc.

pH adjusting agents: for example, hydrochloric acid, sodium hydroxide, potassium hydroxide, calcium hydroxide, magnesium hydroxide, triethanolamine, monoethanolamine, diisopropanolamine, sulfuric acid, phosphoric acid, etc.

Tonicity agents: for example, sodium bisulfite, sodium sulfite, potassium chloride, calcium chloride, sodium chloride, magnesium chloride, potassium acetate, sodium acetate, sodium bicarbonate, sodium carbonate, sodium thiosulfate, magnesium sulfate, disodium hydrogen phosphate, sodium dihydrogen phosphate, potassium dihydrogen phosphate, glycerin, propylene glycol, etc.

Chelating agents: for example, ascorbic acid, edetic acid tetrasodium, sodium edetate, citric acid, etc.

Buffering agents: for example, phosphate buffering agents; citrate buffering agents such as citric acid and sodium citrate; acetate buffering agents such as acetic acid, potassium acetate, and sodium acetate; carbonate buffering agents such as sodium bicarbonate and sodium carbonate; borate buffering agents such as boric acid and borax; amino acid buffering agents such as taurine, aspartic acid and its salts (e.g., potassium salts etc.), and $\epsilon$-aminocaproic acid; etc.

Among the above, phosphate buffering agents are preferred for pH adjustment and the use of a phosphate buffering agent reduces adsorption of GGA to a container wall, thereby reducing the loss of the GGA content of the ophthalmic agent. The use of a phosphate buffering agent also reduces white turbidity during storage at low temperature, reduces adsorption of GGA to a contact lens, and improves the thermal and light stabilities.

The phosphate buffering agents can be used alone or in combination of two or more thereof.

The phosphate buffering agent is not particularly limited and examples thereof include phosphoric acid; alkali metal phosphates such as disodium hydrogen phosphate, sodium dihydrogen phosphate, trisodium phosphate, dipotassium hydrogen phosphate, potassium dihydrogen phosphate, and tripotassium phosphate; alkaline earth metal phosphates such as calcium phosphate, calcium hydrogen phosphate, calcium dihydrogen phosphate, monomagnesium phosphate, dimagnesium phosphate (magnesium hydrogen phosphate), and trimagnesium phosphate; and ammonium phosphates such as diammonium hydrogen phosphate and ammonium dihydrogen phosphate. The phosphate buffering agent may be an anhydride or hydrate.

Among the above, preferably at least one selected from the group consisting of phosphoric acid and alkali metal phosphates is used, and more preferably at least one selected from the group consisting of phosphoric acid and sodium phosphates is used.

Preferred combinations of phosphate buffering agents are, for example, a combination of phosphoric acid, disodium hydrogen phosphate, sodium dihydrogen phosphate, and trisodium phosphate; a combination of phosphoric acid, disodium hydrogen phosphate, and sodium dihydrogen phosphate; a combination of phosphoric acid, disodium hydrogen phosphate, and trisodium phosphate; a combination of phosphoric acid, sodium dihydrogen phosphate, and trisodium phosphate; a combination of disodium hydrogen phosphate, sodium dihydrogen phosphate, and trisodium phosphate; a combination of phosphoric acid and disodium hydrogen phosphate; a combination of phosphoric acid and sodium dihydrogen phosphate; a combination of phosphoric acid and trisodium phosphate; a combination of disodium hydrogen phosphate and sodium dihydrogen phosphate; a combination of disodium hydrogen phosphate and trisodium phosphate; and a combination of sodium dihydrogen phosphate and trisodium phosphate.

Among these, preferred are a combination of phosphoric acid, disodium hydrogen phosphate, and sodium dihydrogen phosphate; a combination of phosphoric acid and disodium hydrogen phosphate; a combination of phosphoric acid and sodium dihydrogen phosphate; and a combination of disodium hydrogen phosphate and sodium dihydrogen phosphate. More preferred is a combination of disodium hydrogen phosphate and sodium dihydrogen phosphate.

The phosphate buffering agent content expressed in terms of a corresponding anhydride is preferably 0.001% by weight or more, more preferably 0.005% by weight or more, further more preferably 0.01% by weight or more, further more preferably 0.05% by weight or more, relative to the total amount of the ophthalmic agent. The phosphate buffering agent in the above ranges is sufficient to exhibit the effects of stabilizing GGA, reducing white turbidity at low temperature, and reducing adsorption of GGA to a container wall or a contact lens.

The phosphate buffering agent content of the ophthalmic agent expressed in terms of a corresponding anhydride is preferably 10% by weight or less, more preferably 7% by weight or less, further more preferably 5% by weight or less, further more preferably 3% by weight or less, relative to the total amount of the ophthalmic agent. When GGA is in the above ranges, the ophthalmic agent exhibits reduced eye irritancy.

The phosphate buffering agent content expressed in terms of a corresponding anhydride is, for example, about 0.001 to 10% by weight, about 0.001 to 7% by weight, about 0.001 to 5% by weight, about 0.001 to 3% by weight, about 0.005 to 10% by weight, about 0.005 to 7% by weight, about 0.005 to 5% by weight, about 0.005 to 3% by weight, about 0.01 to 10% by weight, about 0.01 to 7% by weight, about 0.01 to 5% by weight, about 0.01 to 3% by weight, about 0.05 to 10% by weight, about 0.05 to 7% by weight, about 0.05 to 5% by weight, or about 0.05 to 3% by weight, relative to the total amount of the ophthalmic agent.

The phosphate buffering agent content expressed in terms of a corresponding anhydride is preferably 0.0005 parts by weight or more, more preferably 0.001 parts by weight or more, further more preferably 0.005 parts by weight or more, further more preferably 0.01 parts by weight or more, relative to 1 part by weight of GGA. The phosphate buffering agent in the above ranges is sufficient to exhibit the effects of stabilizing GGA, reducing white turbidity at low temperature, and reducing adsorption of GGA to a container wall or a contact lens.

The phosphate buffering agent content expressed in terms of a corresponding anhydride is preferably 5000 parts by weight or less, more preferably 1000 parts by weight or less, further more preferably 500 parts by weight or less, further more preferably 200 parts by weight or less, relative to 1 part by weight of GGA. When the phosphate buffering agent is in the above ranges, the ophthalmic agent exhibits reduced eye irritancy.

The phosphate buffering agent content expressed in terms of a corresponding anhydride is, for example, about 0.0005 to 5000 parts by weight, about 0.0005 to 1000 parts by weight, about 0.0005 to 500 parts by weight, about 0.0005 to 200 parts by weight, about 0.001 to 5000 parts by weight, about 0.001 to 1000 parts by weight, about 0.001 to 500 parts by weight, about 0.001 to 200 parts by weight, about 0.005 to 5000 parts by weight, about 0.005 to 1000 parts by weight, about 0.005 to 500 parts by weight, about 0.005 to 200 parts by weight, about 0.01 to 5000 parts by weight, about 0.01 to 1000 parts by weight, about 0.01 to 500 parts by weight, or about 0.01 to 200 parts by weight, relative to 1 part by weight of GGA.

Stabilizers: for example, trometamol, sodium formaldehyde sulfoxylate (rongalit), tocopherol, sodium pyrosulfite, monoethanolamine, aluminum monostearate, glyceryl monostearate, etc.

Antioxidants: for example, water-soluble antioxidants such as ascorbic acid, ascorbic acid derivatives (ascorbic acid-2-sulfate disodium salts, sodium ascorbate, ascorbic acid-2-magnesium phosphate, ascorbic acid-2-sodium phosphate, etc.), sodium bisulfite, sodium sulfite, sodium thiosulfate, etc.

The ophthalmic agent may comprise a fat-soluble antioxidant and the use of a fat-soluble antioxidant reduces adsorption of the ophthalmic agent to a container wall, thereby reducing the loss of the GGA content of the composition. The use of a fat-soluble antioxidant also reduces adsorption of GGA to a contact lens, and improves the thermal and light stabilities of GGA.

Examples of the fat-soluble antioxidant include butyl group-containing phenols such as butylhydroxytoluene (BHT) and butylhydroxyanisole (BHA); nordihydroguaiaretic acid (NDGA); ascorbic acid esters such as ascorbyl palmitate, ascorbyl stearate, ascorbyl aminopropyl phosphate, ascorbyl tocopherol phosphate, ascorbic acid triphosphate, and ascorbyl palmitate phosphate; tocopherols such as α-tocopherol, β-tocopherol, γ-tocopherol, and δ-tocopherol; tocopherol derivatives such as tocopherol acetate, tocopherol nicotinate, and tocopherol succinate; gallic acid esters such as ethyl gallate, propyl gallate, octyl gallate, and dodecyl gallate; propyl gallate; 3-butyl-4-hydroxyquinolin-2-one; vegetable oils such as soybean oil, rapeseed oil, olive oil, and sesame oil; carotenoids such as lutein and astaxanthin; polyphenols such as anthocyanins, catechin, tannin, and curcumin; the vitamin A group including retinol, retinol esters (retinol acetate, retinol propionate, retinol butyrate, retinol octylate, retinol laurate, retinol stearate, retinol myristate, retinol oleate, retinol linolenate, retinol linoleate, retinol palmitate, etc.), retinal, retinal esters (retinal acetate, retinal propionate, retinal palmitate, etc.), retinoic acid, retinoic acid esters (methyl retinoate, ethyl retinoate, retinal retinoate, tocopheryl retinoate, etc.), dehydro forms of retinol, dehydro forms of retinal, dehydro forms of retinoic acid, provitamin A (α-carotene, β-carotene, γ-carotene, δ-carotene, lycopene, zeaxanthin, β-cryptoxanthin, echinenone, etc.), and vitamin A; CoQ10, etc. These compounds are marketed.

Among these, preferred are butyl group-containing phenols, NDGA, ascorbic acid esters, tocopherols, tocopherol derivatives, gallic acid esters, propyl gallate, and 3-butyl-4-hydroxyquinolin-2-one, vegetable oils, and the vitamin A group. Among these, preferred are butyl group-containing phenols, tocopherols, tocopherol derivatives, vegetable oils, and the vitamin A group, more preferred are butyl group-containing phenols, vegetable oils, retinol, and retinol esters, and further more preferred are BHT, BHA, sesame oil, and retinol palmitate.

These fat-soluble antioxidants can be used alone or in combination of two or more thereof.

The fat-soluble antioxidant content of the ophthalmic agent is preferably 0.00001% by weight or more, more preferably 0.00005% by weight or more, further more preferably 0.0001% by weight or more, further more preferably 0.0005% by weight or more, relative to the total amount of the ophthalmic agent. The fat-soluble antioxidant in the above ranges is sufficient to exhibit the effects of reducing adsorption of GGA to a container wall (thereby reducing the loss of the GGA content), reducing adsorption of GGA to a contact lens, and improving the thermal and light stabilities of GGA.

The fat-soluble antioxidant content of the ophthalmic agent is preferably 10% by weight or less, more preferably 5% by weight or less, further more preferably 2% by weight or less, further more preferably 1% by weight or less, relative to the total amount of the composition. When the fat-soluble antioxidant is in the above ranges, the ophthalmic agent exhibits reduced eye irritancy.

The fat-soluble antioxidant content of the ophthalmic agent is, for example, about 0.00001 to 10% by weight, about 0.00001 to 5% by weight, about 0.00001 to 2% by weight, about 0.00001 to 1% by weight, about 0.00005 to 10% by weight, about 0.00005 to 5% by weight, about 0.00005 to 2% by weight, about 0.00005 to 1% by weight, about 0.0001 to 10% by weight, about 0.0001 to 5% by weight, about 0.0001 to 2% by weight, about 0.0001 to 1% by weight, about 0.0005 to 10% by weight, about 0.0005 to 5% by weight, about 0.0005 to 2% by weight, or about 0.0005 to 1% by weight, relative to the total amount of the ophthalmic agent.

The fat-soluble antioxidant content of the ophthalmic agent is preferably 0.0001 parts by weight or more, more preferably 0.001 parts by weight or more, further more preferably 0.005 parts by weight or more, further more preferably 0.01 parts by weight or more, relative to 1 part by weight of GGA. The fat-soluble antioxidant in the above ranges is sufficient to exhibit the effects of reducing adsorption of GGA to a container wall (thereby reducing the loss of the GGA content), reducing adsorption of GGA to a contact lens, and improving the thermal and light stabilities of GGA.

The fat-soluble antioxidant content of the ophthalmic agent is preferably 100 parts by weight or less, more preferably 50 parts by weight or less, further more preferably 10 parts by weight or less, further more preferably 5 parts by weight or less, relative to 1 part by weight of GGA. When the fat-soluble antioxidant is in the above ranges, the ophthalmic agent exhibits reduced eye irritancy.

The fat-soluble antioxidant content of the ophthalmic agent is, for example, about 0.0001 to 100 parts by weight, about 0.0001 to 50 parts by weight, about 0.0001 to 10 parts by weight, about 0.0001 to 5 parts by weight, about 0.001 to 100 parts by weight, about 0.001 to 50 parts by weight, about 0.001 to 10 parts by weight, about 0.001 to 5 parts by weight, about 0.005 to 100 parts by weight, about 0.005 to 50 parts by weight, about 0.005 to 10 parts by weight, about 0.005 to 5 parts by weight, about 0.01 to 100 parts by weight, about 0.01 to 50 parts by weight, about 0.01 to 10 parts by weight, or about 0.01 to 5 parts by weight, relative to 1 part by weight of GGA.

Thickening agents: for example, guar gum; hydroxypropyl guar gum; high molecular cellulose compounds such as methylcellulose, ethylcellulose, hydroxypropyl methylcellulose, hydroxyethyl cellulose, and carboxymethyl cellulose sodium; gum arabic; karaya gum; xanthan gum; agar-agar; alginic acid; α-cyclodextrin; dextrin; dextran; heparin; heparinoid; heparin sulfate; heparan sulfate; hyaluronic acid; hyaluronates (sodium salts etc.); sodium chondroitin sulfate; starch; chitin and its derivatives; chitosan and its derivatives; carrageenan; sorbitol; high molecular polyvinyl compounds such as polyvinylpyrrolidone, polyvinyl alcohol, and polyvinyl methacrylate; carboxy vinyl polymers such as alkali metal polyacrylates (sodium salts, potassium salts, etc.), amine polyacrylates (monoethanolamine salts, diethanolamine salts, triethanolamine salts, etc.), and ammonium polyacrylates; casein; gelatin; collagen; pectin; elastin; ceramide; liquid paraffin; glycerin; polyethylene glycol; macrogol; polyethyleneimine alginates (sodium salts etc.); alginate esters (propylene glycol esters etc.); powdered tragacanth; triisopropanolamine; etc.

<Other Prophylactic, Ameliorating or Therapeutic Components for Retinal Diseases>

Preferably the ophthalmic agent comprises, in addition to GGA, a component that prevents or treats a retinal disease with a different mechanism of action from that of GGA. That is, the ophthalmic agent preferably comprises a combination of GGA and another component as active ingredients for preventing, ameliorating or treating a retinal disease. Such components that prevent or treat a retinal disease with a different mechanism of action from that of GGA can be used alone or in combination of two or more thereof.

Examples of such a combination include, but are not limited to, combinations of GGA and a prostaglandin F2α derivative, such as combinations of GGA and a prost drug (GGA and latanoprost, GGA and travoprost, GGA and tafluprost, etc.), combinations of GGA and a prostamide drug (GGA and bimatoprost, etc.), and combinations of GGA and a prostone drug (GGA and isopropyl unoprostone); combinations of GGA and a sympatholytic agent such as, combinations of GGA and a β-blocker (GGA and timolol maleate, GGA and gel-forming timolol, GGA and carteolol hydrochloride, GGA and gel-forming carteolol, etc.), combinations of GGA and a β1-blocker (GGA and betaxolol hydrochloride, etc.), combinations of GGA and an αβ-blocker (GGA and levobunolol hydrochloride, GGA and nipradilol, GGA and bunazosin hydrochloride, etc.), and combinations of GGA and an α2-blocker (GGA and brimonidine tartrate); combinations of GGA and a parasympathomimetic drug, such as GGA and pilocarpine hydrochloride, and GGA and distigmine bromide; combinations of GGA and a sympathomimetic drug, such as GGA and epinephrine, GGA and epinephrine bitartrate, and GGA and dipivefrin hydrochloride; combinations of GGA and a carbonic anhydrase inhibitor, such as GGA and dorzolamide hydrochloride, and GGA and brinzolamide; combinations of GGA and a specific inhibitor to ROCK (Rho-associated coiled coil forming protein kinase), such as GGA and SNJ-1656, and GGA and K-115; combinations of GGA and a calcium antagonist, such as GGA and lomerizine hydrochloride; combinations of GGA and an EP2 agonist, such as GGA and DE-117; combinations of GGA and an adenosine A2a receptor agonist, such as GGA and OPA-6566; combinations of GGA and a therapeutic agent for age-related macular degeneration, such as combinations of GGA and a VEGF aptamer (GGA and pegaptanib sodium) and combinations of GGA and a VEGF inhibitor (GGA and ranibizumab, and GGA and bevacizumab).

Among these, preferred are combinations of GGA and a prostaglandin F2α derivative and combinations of GGA and a sympatholytic drug (especially preferred are combinations of GGA and a β-blocker) because these combinations exhibit a very high prophylactic, ameliorating or therapeutic effect for a retinal disease.

<Other Pharmacologically or Physiologically Active Components>

The ophthalmic agent can comprise a pharmacologically or physiologically active component other than the prophylactic, ameliorating or therapeutic component for a retinal disease. Such pharmacologically or physiologically active components can be used alone or in combination of two or more thereof.

Examples of the pharmacologically or physiologically active components include nerve growth factors, decongestants, drugs for restoring extraocular muscle function, anti-inflammatory drugs or astringent drugs, antihistaminics or antiallergics, vitamins, amino acids, antibacterial drugs or bactericides, sugars, high molecular compounds, celluloses or their derivatives, local anesthetics, etc. These drugs will be exemplified below.

Nerve growth factors: for example, nerve growth factor (NGF), brain-derived nerve growth factor (BDNF), glial cell line-derived neurotrophic factor (GDNF), etc.

Since nutritional factors including nerve growth factors are contained in serum, it is possible to add serum from a patient to a preparation for the patient.

Decongestants: for example, α-adrenergic agonists such as epinephrine, epinephrine hydrochloride, ephedrine hydrochloride, oxymetazoline hydrochloride, tetrahydrozoline hydrochloride, naphazoline hydrochloride, phenylephrine hydrochloride, methylephedrine hydrochloride, epinephrine hydrogen tartrate, naphazoline nitrate, etc. These may be in the d-form, l-form, or dl-form.

Drugs for restoring extraocular muscle function: for example, cholinesterase inhibitors having an active center similar to that of acetylcholine, such as neostigmine methylsulfate, tropicamide, helenien, atropine sulfate, etc.

Anti-inflammatory drugs or astringent drugs: for example, zinc sulfate, zinc lactate, allantoin, ϵ-aminocaproic acid, indomethacin, lysozyme chloride, silver nitrate, pranoprofen, azulene sulfonate sodium, dipotassium glycyrrhizinate, diammonium glycyrrhizinate, diclofenac sodium, bromfenac sodium, berberine chloride, berberine sulfate, etc.

Antihistaminics or antiallergics: for example, acitazanolast, diphenhydramine or its salts (hydrochloride etc.), chlorpheniramine maleate, ketotifen fumarate, levocabastine or its salts (hydrochloride etc.), amlexanox, ibudilast, tazanolast, tranilast, oxatomide, suplatast or its salts (tosilate etc.), sodium cromoglicate, pemirolast potassium, etc.

Vitamins: for example, retinol acetate, retinol palmitate, pyridoxine hydrochloride, flavin adenine dinucleotide sodium, pyridoxal phosphate, cyanocobalamin, panthenol, calcium pantothenate, sodium pantothenate, ascorbic acid, tocopherol acetate, tocopherol nicotinate, tocopherol succinate, tocopherol calcium succinate, ubiquinone derivatives, etc.

Amino acids: for example, aminoethylsulfonic acid (taurine), glutamic acid, creatinine, sodium aspartate, potassium aspartate, magnesium aspartate, magnesium potassium aspartate, sodium glutamate, magnesium glutamate, ϵ-aminocaproic acid, glycine, alanine, arginine, lysine, γ-aminobutyric acid, γ-aminovaleric acid, sodium chondroitin sulfate, etc. These may be in the d-form, l-form, or dl-form.

Antibacterial drugs or bactericides: for example, alkylpolyaminoethylglycine, chloramphenicol, sulfamethoxazole, sulfisoxazole, sulfamethoxazole sodium, sulfisoxazole diethanolamine, sulfisoxazole monoethanolamine, sulfisomezole sodium, sulfisomidine sodium, ofloxacin, norfloxacin, levofloxacin, lomefloxacin hydrochloride, acyclovir, etc.

Sugars: for example, monosaccharides, disaccharide, in particular, glucose, maltose, trehalose, sucrose, cyclodextrin, xylitol, sorbitol, mannitol, etc.

High molecular compounds: for example, alginic acid, sodium alginate, dextrin, dextran, pectin, hyaluronic acid, chondroitin sulfate, (completely or partially saponified) polyvinyl alcohol, polyvinylpyrrolidone, carboxy vinyl polymers, macrogol, pharmaceutically acceptable salts thereof, etc.

Celluloses or their derivatives: for example, ethylcellulose, hydroxyethyl cellulose, hydroxypropyl cellulose, hydroxypropyl methylcellulose, methylcellulose, carboxymethyl cellulose, carboxymethylcellulose sodium, carboxyethyl cellulose, nitrocellulose, etc.

Local anesthetics: for example, chlorobutanol, procaine hydrochloride, lidocaine hydrochloride, etc.

<GGA Content>

In the case of the ophthalmic preparation in the form other than a solid, for example, a liquid, a fluid, a gel, or a semi-solid, the GGA content of the ophthalmic composition is preferably 0.00001% by weight or more, more preferably 0.0001% by weight or more, further more preferably 0.001% by weight or more, relative to the total amount of the composition. The GGA content may be 0.01% by weight or more, 0.1% by weight or more, or 1% by weight or more. GGA in the above ranges is sufficient to exhibit the prophylactic, ameliorating or therapeutic effect for a retinal disease.

In the above case of the ophthalmic preparation in the form other than a solid, for example, a liquid, a fluid, a gel, or a semi-solid, the GGA content of the ophthalmic composition is preferably 10% by weight or less, more preferably 5% by weight or less, further more preferably 3% by weight or less, relative to the total amount of the composition. GGA in the above ranges is sufficient to exhibit the prophylactic, ameliorating or therapeutic effect for a retinal disease, and the ophthalmic preparation comprising GGA in the above ranges allows clear vision and hardly causes blurred vision.

In the above case of the ophthalmic preparation in the form other than a solid, for example, a liquid, a fluid, a gel, or a semi-solid, the GGA content of the ophthalmic composition is, for example, about 0.00001 to 10% by weight, about 0.00001 to 5% by weight, about 0.00001 to 3% by weight, about 0.0001 to 10% by weight, about 0.0001 to 5% by weight, about 0.0001 to 3% by weight, about 0.001 to 10% by weight, about 0.001 to 5% by weight, about 0.001 to 3% by weight, about 0.01 to 10% by weight, about 0.01 to 5% by weight, about 0.01 to 3% by weight, about 0.1 to 10% by weight, about 0.1 to 5% by weight, about 0.1 to 3% by weight, about 1 to 10% by weight, about 1 to 5% by weight, or about 1 to 3% by weight, relative to the total amount of the composition.

The GGA content of a solid preparation such as a sustained-release intraocular implant preparation and a sustained-release contact lens preparation impregnated with GGA will be described later.

pH

When the ophthalmic agent is a composition containing moisture, the pH of the ophthalmic agent is preferably 4 or higher, more preferably 5.5 or higher, further more preferably 6 or higher, further more preferably 6.5 or higher. The preparation having a pH value in the above ranges is excellent in the thermal and light stabilities of GGA.

The pH of the ophthalmic agent is preferably 9 or lower, more preferably 8.5 or lower, further more preferably 8 or lower, further more preferably 7.5 or lower. The ophthalmic agent having a pH value in the above ranges exhibits reduced eye irritancy.

Sustained-Release Intraocular Implant

A sustained-release intraocular implant is another example of the ophthalmic agent. Such a sustained-release intraocular implant can be prepared by various known preparation methods. The sustained-release intraocular implant prepared by known methods are, for example, a matrix preparation prepared by mixing GGA with a carrier containing a high molecular material and forming the mixture into a particular shape, a preparation prepared by coating a core containing GGA with a high molecular membrane, a capsule preparation prepared by filling GGA into a minute capsule made of a high molecular material, etc.

As the high molecular material, any high molecular material can be used without limitation as long as it is usually used for a sustained-release intraocular implant. Examples of such a high molecular material include hydroxypropyl cellulose, hydroxypropyl methylcellulose, hydroxypropyl methylcellulose phthalate, pullulan, gelatin, collagen, atelocollagen, hyaluronic acid, casein, agar-agar, gum arabic, dextrin, ethylcellulose, methylcellulose, chitin, chitosan, mannan, carboxymethyl ethyl cellulose, carboxymethyl cellulose sodium, polyethylene glycol, sodium alginate, polyvinyl alcohol, cellulose acetate, polyvinylpyrrolidone, silicone, polyvinyl acetal diethylamino acetate, albumin, lactic acid-glycolic acid copolymers, etc.

These high molecular materials can be used alone or in combination of two or more thereof.

Preferably the sustained-release intraocular implant comprises GGA and another prophylactic, ameliorating or therapeutic component for a retinal disease. Such a combination is exemplified above. The sustained-release intraocular implant can further comprise another pharmacologically or physiologically active component. Such a component is exemplified above.

The GGA content of the sustained-release intraocular implant is preferably 0.001 mg or more, more preferably 0.01 mg or more, further more preferably 0.1 mg or more, relative to the total amount of the preparation. The GGA content is preferably 1000 mg or less, more preferably 100 mg or less, further more preferably 10 mg or less. GGA in the above ranges is sufficient to exhibit the prophylactic, ameliorating or therapeutic effect for a retinal disease.

The GGA content of the sustained-release intraocular implant is, for example, about 0.001 to 1000 mg, about 0.001 to 100 mg, about 0.001 to 10 mg, about 0.01 to 1000 mg, about 0.01 to 100 mg, about 0.01 to 10 mg, about 0.1 to 1000 mg, about 0.1 to 100 mg, or about 0.1 to 10 mg, relative to the total amount of the preparation.

Sustained-Release Contact Lens Preparation

A sustained-release contact lens preparation in which the contact lens itself comprises GGA is another example of the ophthalmic agent. Such a sustained-release preparation can be prepared by, for example, immersing a contact lens in a contact lens solution containing GGA, the contact lens solution being exemplified by a washing solution, a storage solution, a sterilizing solution, a multipurpose solution, and a package solution, etc. Alternatively, GGA may be impregnated into a raw material for producing a contact lens, for example, a constituent monomer (hydroxyethyl methacrylate, methyl methacrylate, vinylpyrrolidone, divinylbenzene, methacrylic acid, ethylene glycol dimethacrylate, benzoin methyl ether, etc.) of a contact lens polymer, a colorant, or an ultraviolet absorber, and with the use of these, the sustained-release contact lens can be prepared.

The GGA content of the sustained-release contact lens preparation is preferably 0.001 mg or more, more preferably 0.01 mg or more, further more preferably 0.1 mg or more, relative to the total amount of the preparation. The GGA content is preferably 1000 mg or less, more preferably 100 mg or less, further more preferably 10 mg or less. GGA in the above ranges is sufficient to exhibit the prophylactic, ameliorating or therapeutic effect for a retinal disease.

The GGA content of the sustained-release contact lens preparation is, for example, about 0.001 to 1000 mg, about 0.001 to 100 mg, about 0.001 to 10 mg, about 0.01 to 1000 mg, about 0.01 to 100 mg, about 0.01 to 10 mg, about 0.1 to 1000 mg, about 0.1 to 100 mg, or about 0.1 to 10 mg, relative to the total amount of the preparation.

Preferably the sustained-release contact lens preparation comprises GGA and another prophylactic, ameliorating or therapeutic component for a retinal disease. Such a combination is exemplified above. The sustained-release contact lens preparation can further comprise a pharmacologically or physiologically active component other than GGA. Such a component is exemplified above.

The dosage form of the ophthalmic agent is preferably an eye drop, an intraocular injection, an ophthalmic ointment, or an eye wash and is more preferably an eye drop because of their good penetration into an affected site.

(2) Oral Agent

GGA can be formulated into an oral agent or orally administered drug. Examples of the oral agent include, but are not limited to, solid preparations such as tablets (including sublingual tablets and orally disintegrating tablets), capsules (including soft capsules and microcapsules), granules, powders, tablet agents, chewable tablets, and troches; liquid preparations such as syrups, emulsions, and suspensions; etc.

The solid preparation can be prepared by mixing GGA with a pharmaceutically acceptable carrier, and as needed a pharmaceutically acceptable additive for an oral agent and a pharmacologically or physiologically active component other than GGA in accordance with a known method, for example, a method described in the Japanese Pharmacopoeia.

Examples of the pharmaceutically acceptable carrier include, but are not limited to, excipients such as lactose, saccharose, D-mannitol, D-sorbitol, starch, pregelatinized starch, dextrin, crystalline cellulose, low-substituted hydroxypropyl cellulose, carboxymethyl cellulose sodium, gum arabic, pullulan, light anhydrous silicic acid, synthetic aluminum silicate, and magnesium aluminometasilicate; binders such as pregelatinized starch, sucrose, gelatin, gum arabic, methylcellulose, carboxymethyl cellulose, carboxymethylcellulose sodium, crystalline cellulose, saccharose, D-mannitol, trehalose, dextrin, pullulan, hydroxypropyl cellulose, hydroxypropyl methylcellulose, and polyvinylpyrrolidone; disintegrants such as lactose, saccharose, starch, carboxymethyl cellulose, carboxymethyl cellulose calcium, croscarmellose sodium, carboxymethyl starch sodium, light anhydrous silicic acid, and low-substituted hydroxypropyl cellulose; stabilizers such as anhydrous citric acid, sodium laurate, and glycerol; etc.

The liquid preparation can also be prepared by a known method, for example, a method described in the Japanese Pharmacopoeia. For example, the liquid preparation can be prepared by dissolving or dispersing GGA in water, ethanol, glycerin, simple syrup, or a mixture thereof.

To the oral agent may be added an additive for an oral agent, such as a sweetener, an antiseptic, a lubricant, a diluent, a buffering agent, an aromatizing agent, a colorant, and an antioxidant.

Preferably the oral agent comprises GGA in combination with a component that prevents or treats a retinal disease with a different mechanism of action from that of the agent of the present invention. Examples of such a combination include, but are not limited to, combinations of GGA and a carbonic anhydrase inhibitor, such as GGA and acetazolamide, GGA and methazolamide, and GGA and diclofenamide; combinations of GGA and a hyperosmotic drug, such as GGA and concentrated glycerin, and GGA and isosorbide; etc.

Among these, preferred are combinations of GGA and a carbonic anhydrase inhibitor, more preferred are a combination of GGA and acetazolamide and a combination of GGA and methazolamide, and further more preferred is a combination of GGA and methazolamide.

Such components that prevent or treat a retinal disease with a different mechanism of action from that of GGA can be used alone or in combination of two or more thereof.

The oral agent can comprise a pharmacologically or physiologically active component other than the prophylactic, ameliorating or therapeutic component for a retinal disease.

Examples of such a known pharmacologically or physiologically active component include nerve growth factors, decongestants, drugs for restoring extraocular muscle function, anti-inflammatory drugs or astringent drugs, antihistaminics or antiallergics, vitamins, amino acids, antibacterial drugs or bactericides, etc.

The GGA content of the oral agent in the form of a solid preparation is preferably 0.001% by weight or more, more preferably 0.01% by weight or more, furthermore preferably 0.1% by weight or more, relative to the total amount of the composition. The GGA content is preferably 80% by weight or less, more preferably 60% by weight or less, further more preferably 50% by weight or less.

The GGA content of the oral agent in the form of a solid preparation is, for example, about 0.001 to 80% by weight, about 0.001 to 60% by weight, about 0.001 to 50% by weight, about 0.01 to 80% by weight, about 0.01 to 60% by weight, about 0.01 to 50% by weight, about 0.1 to 80% by weight, about 0.1 to 60% by weight, or about 0.1 to 50% by weight, relative to the total amount of the preparation.

The GGA content of the oral agent in the form of a liquid preparation is preferably about 0.001% by weight or more, more preferably about 0.01% by weight or more, further more preferably about 0.1% by weight or more, relative to the total amount of the composition. The GGA content is preferably about 80% by weight or less, more preferably about 60% by weight or less, further more preferably about 50% by weight or less.

The GGA content of the oral agent in the form of a liquid preparation is, for example, about 0.001 to 80% by weight, about 0.001 to 60% by weight, about 0.001 to 50% by weight, about 0.01 to 80% by weight, about 0.01 to 60% by weight, about 0.01 to 50% by weight, about 0.1 to 80% by weight, about 0.1 to 60% by weight, or about 0.1 to 50% by weight, relative to the total amount of the preparation.

GGA in the above ranges is sufficient to exhibit the prophylactic, ameliorating or therapeutic effect for a retinal disease.

In the oral agent, the carriers, the additives, and the pharmacologically or physiologically active components other than GGA can be used alone or in combination of two or more thereof.

(3) Injection

An injection can be prepared by dissolving or dispersing GGA in water for injection or physiological saline in accordance with a known method, for example, a method described in the Japanese Pharmacopoeia. The injection may comprise a pharmaceutically acceptable carrier such as a solubilizing agent, a suspending agent, a tonicity agent, a buffering agent, a soothing agent, a stabilizer, an antiseptic, etc. and may further comprise a pharmaceutically acceptable additive for an injection.

Preferably the injection comprises, in addition to GGA, a component that prevents or treats a retinal disease with a different mechanism of action from that of GGA. That is, the injection preferably comprises a combination of GGA and another component as active ingredients for preventing, ameliorating or treating a retinal disease. Such components that prevent or treat a retinal disease with a different mechanism of action from that of GGA can be used alone or in combination of two or more thereof.

Examples of such a combination include, but are not limited to, combinations of GGA and a prostaglandin F2α derivative, such as combinations of GGA and a prost drug (GGA and latanoprost, GGA and travoprost, GGA and tafluprost, etc.), combinations of GGA and a prostamide drug (GGA and bimatoprost, etc.), and combinations of GGA and a prostone drug (GGA and isopropyl unoprostone); combinations of GGA and a sympatholytic agent such as, combinations of GGA and a β-blocker (GGA and timolol maleate, GGA and gel-forming timolol, GGA and carteolol hydrochloride, GGA and gel-forming carteolol, etc.), combinations of GGA and a β1-blocker (GGA and betaxolol hydrochloride, etc.), combinations of GGA and an αβ-blocker (GGA and levobunolol hydrochloride, GGA and nipradilol, GGA and bunazosin hydrochloride, etc.), and combinations of GGA and an α2-blocker (GGA and brimonidine tartrate); combinations of GGA and a parasympathomimetic drug, such as GGA and pilocarpine hydrochloride, and GGA and distigmine bromide; combinations of GGA and a sympathomimetic drug, such as GGA and epinephrine, GGA and epinephrine bitartrate, and GGA and dipivefrin hydrochloride; combinations of GGA and a carbonic anhydrase inhibitor, such as GGA and dorzolamide hydrochloride, and GGA and brinzolamide; combinations of GGA and a specific inhibitor to ROCK (Rho-associated coiled coil forming protein kinase), such as GGA and SNJ-1656, and GGA and K-115; combinations of GGA and a calcium antagonist, such as GGA and lomerizine hydrochloride; combinations of GGA and an EP2 agonist, such as GGA and DE-117; combinations of GGA and an adenosine A2a receptor agonist, such as GGA and OPA-6566; combinations of GGA and a therapeutic agent for age-related macular degeneration, such as combinations of GGA and a VEGF aptamer (GGA and pegaptanib sodium) and combinations of GGA and a VEGF inhibitor (GGA and ranibizumab, and GGA and bevacizumab).

Among these, preferred are combinations of GGA and a prostaglandin F2α derivative and combinations of GGA and a sympatholytic drug (especially preferred are combinations of GGA and a β-blocker) because these combinations exhibit a very high prophylactic, ameliorating or therapeutic effect for a retinal disease.

The injection can comprise a pharmacologically or physiologically active component other than the prophylactic, ameliorating or therapeutic component for a retinal disease. Examples of the pharmacologically or physiologically active component include nerve growth factors, decongestants, drugs for restoring extraocular muscle function, anti-inflammatory drugs or astringent drugs, antihistaminics or antiallergics, vitamins, amino acids, antibacterial drugs or bactericides, etc.

The GGA content of the injection is preferably 0.001% by weight or more, more preferably 0.01% by weight or more, further more preferably 0.1% by weight or more, relative to the total amount of the preparation. The GGA content is preferably 80% by weight or less, more preferably 60% by weight or less, further more preferably 50% by weight or less. GGA in the above ranges is sufficient to exhibit the prophylactic, ameliorating or therapeutic effect for a retinal disease.

The GGA content of the injection is, for example, about 0.001 to 80% by weight, about 0.001 to 60% by weight, about 0.001 to 50% by weight, about 0.01 to 80% by weight, about 0.01 to 60% by weight, about 0.01 to 50% by weight, about 0.1 to 80% by weight, about 0.1 to 60% by weight, or about 0.1 to 50% by weight, relative to the total amount of the preparation.

In the injection, the additives and the pharmacologically or physiologically active components other than GGA can be used alone or in combination of two or more thereof.

(4) Percutaneous Absorption Agent

A percutaneous absorption agent is exemplified by a liniment prepared by mixing GGA with a (pharmaceutically acceptable) base usually used for a pharmaceutical agent for external use and with a component other than GGA.

Examples of the base include polymers such as sodium alginate, gelatin, corn starch, tragacanth gum, methylcellulose, hydroxyethyl cellulose, carboxymethyl cellulose, xanthan gum, carrageenan, mannan, agarose, dextrin, carboxymethyl starch, polyvinyl alcohol, sodium polyacrylate, methoxyethylene-maleic anhydride copolymers, polyvinyl ethers, polyvinylpyrrolidone, carboxy vinyl polymers, hydroxypropyl cellulose, hydroxypropyl methylcellulose, and pullulan; hydrocarbons such as white petrolatum, yellow petrolatum, paraffin, ceresin wax, and microcrystalline wax; hydrocarbon gels (e.g., Plastibase (trade name), Bristol-Myers Squibb Company); higher fatty acids such as stearic acid; higher alcohols such as cetanol, octyldodecanol, and stearyl alcohol; polyethylene glycols (e.g., macrogol 4000 etc.); polyalcohols such as propylene glycol, glycerin, dipropylene glycol, 1,3-butylene glycol, and concentrated glycerin; fatty acid esters such as monooleic acid esters and stearic acid glycerides; etc. To the percutaneous absorption agent may also be added pharmaceutically acceptable additives for a percutaneous absorption agent, such as a solubilizing agent, an inorganic filler, a moisturizer, an antiseptic, a thickening agent, an antioxidant, and a cooling agent.

The percutaneous absorption agent may be a patch in which a liniment layer comprising GGA is integrated with a support that supports the layer. Methods for preparing such a patch are well known, and examples thereof include a method described in the Japanese Pharmacopoeia.

The percutaneous absorption agent is also exemplified by a patch comprising a liniment layer that is a multilayer laminate in which constituent layers have successively increased level of GGA for the purpose of achieving sustained release of GGA.

The percutaneous absorption agent is also exemplified by a liniment comprising an emulsified particle encapsulating GGA. This liniment can be prepared by mixing GGA with a surfactant (a phospholipid, a nonionic surfactant, etc.), water, and an oily base under agitation. Examples of the oily base include the above-described hydrocarbons, higher fatty acids, higher alcohols, polyalcohols, and fatty acid esters.

The percutaneous absorption agent is also exemplified by a dispersion in which a GGA suspension is dispersed in the form of microparticles in a hydrophobic polymer. Examples of the hydrophobic polymer include, but are not limited to, a polylactic acid.

Preferably the percutaneous absorption agent comprises, in addition to GGA, a component that prevents or treats a retinal disease with a different mechanism of action from that of GGA. That is, the percutaneous absorption agent preferably comprises a combination of GGA and another component as active ingredients for preventing, ameliorating or treating a retinal disease. Such components that prevent or treat a retinal disease with a different mechanism of action from that of GGA can be used alone or in combination of two or more thereof.

Examples of such a combination include, but are not limited to, combinations of GGA and a prostaglandin F2α derivative, such as combinations of GGA and a prost drug (GGA and latanoprost, GGA and travoprost, GGA and tafluprost, etc.), combinations of GGA and a prostamide drug (GGA and bimatoprost, etc.), and combinations of GGA and a prostone drug (GGA and isopropyl unoprostone); combinations of GGA and a sympatholytic agent such as, combinations of GGA and a β-blocker (GGA and timolol maleate, GGA and gel-forming timolol, GGA and carteolol hydrochloride, GGA and gel-forming carteolol, etc.), combinations of GGA and a β1-blocker (GGA and betaxolol hydrochloride, etc.), combinations of GGA and an αβ-blocker (GGA and levobunolol hydrochloride, GGA and nipradilol, GGA and bunazosin hydrochloride, etc.), and combinations of GGA and an α2-blocker (GGA and brimonidine tartrate); combinations of GGA and a parasympathomimetic drug, such as GGA and pilocarpine hydrochloride, and GGA and distigmine bromide; combinations of GGA and a sympathomimetic drug, such as GGA and epinephrine, GGA and epinephrine bitartrate, and GGA and dipivefrin hydrochloride; combinations of GGA and a carbonic anhydrase inhibitor, such as GGA and dorzolamide hydrochloride, and GGA and brinzolamide; combinations of GGA and a specific inhibitor to ROCK (Rho-associated coiled coil forming protein kinase), such as GGA and SNJ-1656, and GGA and K-115; combinations of GGA and a calcium antagonist, such as GGA and lomerizine hydrochloride; combinations of GGA and an EP2 agonist, such as GGA and DE-117; combinations of GGA and an adenosine A2a receptor agonist, such as GGA and OPA-6566; combinations of GGA and a therapeutic agent for age-related macular degeneration, such as combinations of GGA and a VEGF aptamer (GGA and pegaptanib sodium) and combinations of GGA and a VEGF inhibitor (GGA and ranibizumab, and GGA and bevacizumab).

Among these, preferred are combinations of GGA and a prostaglandin F2α derivative and combinations of GGA and a sympatholytic drug (especially preferred are combinations of GGA and a β-blocker) because these combinations exhibit a very high prophylactic, ameliorating or therapeutic effect for a retinal disease.

The percutaneous absorption agent can comprise a pharmacologically or physiologically active component other than the prophylactic, ameliorating or therapeutic component for a retinal disease. Examples of the pharmacologically or physiologically active component include decongestants, drugs for restoring extraocular muscle function, anti-inflammatory drugs or astringent drugs, antihistaminics or antiallergics, vitamins, amino acids, antibacterial drugs or bactericides, etc.

The GGA content of the percutaneous absorption agent is preferably 0.001% by weight or more, more preferably 0.01% by weight or more, furthermore preferably 0.1% by weight or more, relative to the total amount of the preparation. The GGA content is preferably 80% by weight or less, more preferably 60% by weight or less, further more preferably 50% by weight or less. GGA in the above ranges is sufficient to exhibit the prophylactic, ameliorating or therapeutic effect for a retinal disease.

The GGA content of the percutaneous absorption agent is, for example, about 0.001 to 80% by weight, about 0.001 to 60% by weight, about 0.001 to 50% by weight, about 0.01 to 80% by weight, about 0.01 to 60% by weight, about 0.01 to 50% by weight, about 0.1 to 80% by weight, about 0.1 to 60% by weight, or about 0.1 to 50% by weight, relative to the total amount of the preparation.

In the percutaneous absorption, the additives and the pharmacologically or physiologically active components other than GGA can be used alone or in combination of two or more thereof.

(5) Suppository

A suppository can be prepared by mixing GGA with a pharmaceutically acceptable base, for example, an acrylic polymer such as Carbopol and polycarbophil; a cellulose polymer such as hydroxypropyl cellulose and hydroxypropyl methylcellulose; a natural polymer such as sodium alginate and chitosan; a fatty acid wax; etc. in accordance with a known method, for example, a method described in the Japanese Pharmacopoeia.

To the suppository may be added a pharmaceutically acceptable additive for a suppository, for example, an antiseptic such as sodium benzoate, potassium sorbate, and paraben; a pH adjusting agent such as hydrochloric acid, citric acid, and sodium hydroxide; a stabilizer such as methionine; etc.

Preferably the suppository comprises, in addition to GGA, a component that prevents or treats a retinal disease with a different mechanism of action from that of GGA. That is, the suppository preferably comprises a combination of GGA and another component as active ingredients for preventing, ameliorating or treating a retinal disease. Such components that prevent or treat a retinal disease with a different mechanism of action from that of GGA can be used alone or in combination of two or more thereof.

Examples of such a combination include, but are not limited to, combinations of GGA and a prostaglandin F2α derivative, such as combinations of GGA and a prost drug (GGA and latanoprost, GGA and travoprost, GGA and tafluprost, etc.), combinations of GGA and a prostamide drug (GGA and bimatoprost, etc.), and combinations of GGA and a prostone drug (GGA and isopropyl unoprostone); combinations of GGA and a sympatholytic agent such as, combinations of GGA and a β-blocker (GGA and timolol maleate, GGA and gel-forming timolol, GGA and carteolol hydrochloride, GGA and gel-forming carteolol, etc.), combinations of GGA and a β1-blocker (GGA and betaxolol hydrochloride, etc.), combinations of GGA and an αβ-blocker (GGA and levobunolol hydrochloride, GGA and nipradilol, GGA and bunazosin hydrochloride, etc.), and combinations of GGA and an α2-blocker (GGA and brimonidine tartrate); combinations of GGA and a parasympathomimetic drug, such as GGA and pilocarpine hydrochloride, and GGA and distigmine bromide; combinations of GGA and a sympathomimetic drug, such as GGA and epinephrine, GGA and epinephrine bitartrate, and GGA and dipivefrin hydrochloride; combinations of GGA and a carbonic anhydrase inhibitor, such as GGA and dorzolamide hydrochloride, and GGA and brinzolamide; combinations of GGA and a specific inhibitor to ROCK (Rho-associated coiled coil forming protein kinase), such as GGA and SNJ-1656, and GGA and K-115; combinations of GGA and a calcium antagonist, such as GGA and lomerizine hydrochloride; combinations of GGA and an EP2 agonist, such as GGA and DE-117; combinations of GGA and an adenosine A2a receptor agonist, such as GGA and OPA-6566; combinations of GGA and a therapeutic agent for age-related macular degeneration, such as combinations of GGA and a VEGF aptamer (GGA and pegaptanib sodium) and combinations of GGA and a VEGF inhibitor (GGA and ranibizumab, and GGA and bevacizumab).

Among these, preferred are combinations of GGA and a prostaglandin F2α derivative and combinations of GGA and a sympatholytic drug (especially preferred are combinations of GGA and a β-blocker) because these combinations exhibit a very high prophylactic, ameliorating or therapeutic effect for a retinal disease.

The suppository can comprise a pharmacologically or physiologically active component other than the prophylactic, ameliorating or therapeutic component for a retinal disease. Examples of the pharmacologically or physiologically active component include decongestants, drugs for restoring extraocular muscle function, anti-inflammatory drugs or astringent drugs, antihistaminics or antiallergics, vitamins, amino acids, antibacterial drugs or bactericides, etc.

The GGA content of the suppository is preferably 0.001% by weight or more, more preferably 0.01% by weight or more, further more preferably 0.1% by weight or more, relative to the total amount of the preparation. The GGA content is preferably 80% by weight or less, more preferably 60% by weight or less, further more preferably 50% by weight or less. GGA in the above ranges is sufficient to exhibit the prophylactic, ameliorating or therapeutic effect for a retinal disease.

The GGA content of the suppository is, for example, about 0.001 to 80% by weight, about 0.001 to 60% by weight, about 0.001 to 50% by weight, about 0.01 to 80% by weight, about 0.01 to 60% by weight, about 0.01 to 50% by weight, about 0.1 to 80% by weight, about 0.1 to 60% by weight, or about 0.1 to 50% by weight, relative to the total amount of the preparation.

In the suppository, the additives and the pharmacologically or physiologically active components other than GGA can be used alone or in combination of two or more thereof.

(6) Inhalant

An inhalant is exemplified by a powder inhalant, a liquid inhalant, an aerosol, etc. Preparation methods therefor are well known.

A powder inhalant can be prepared by, for example, pulverizing GGA by a conventional method, and as needed mixing with an excipient such as lactose. The powder inhalant can be administered with an inhalator such as Spinhaler (registered trade name).

A liquid inhalant can be prepared by, for example, adding GGA and as needed a pharmaceutically acceptable additive for a liquid inhalant to a pharmaceutically acceptable base such as purified water and water for injection, and dissolving them under stirring. Examples of the pharmaceutically acceptable additive for a liquid inhalant include a tonicity agent such as sodium chloride, a buffering agent such as a borate buffering agent and a phosphate buffering agent, a preservative such as benzalkonium chloride, a thickening agent such as a carboxy vinyl polymer, etc. The liquid inhalant is administered with an inhalator such as nebulizer (registered trade name).

An aerosol can be prepared by, for example, pulverizing GGA by a conventional method, adding a dispersant as needed, and filling them into a spray container with a propellant under cooling. Examples of the propellant include a liquefied hydrofluoroalkane (HFA 134a (1,1,1,2-tetrafluoroethane: $CH_2FCF_3$), HFA 227 (1,1,1,2,3,3,3-heptafluoropropane: $CF_3$—CHF—$CF_3$), etc.) etc. Examples of the dispersant include a medium chain fatty acid triglyceride such as miglyol 812 (trademark) (Dynamit Nobel AG); soybean lecithin; etc.

Preferably the inhalant comprises, in addition to GGA, a component that prevents or treats a retinal disease with a different mechanism of action from that of GGA. That is, the inhalant preferably comprises a combination of GGA and another component as active ingredients for preventing, ameliorating or treating a retinal disease. Such components that prevent or treat a retinal disease with a different mechanism of action from that of GGA can be used alone or in combination of two or more thereof.

Examples of such a combination include, but are not limited to, combinations of GGA and a prostaglandin F2α derivative, such as combinations of GGA and a prost drug (GGA and latanoprost, GGA and travoprost, GGA and tafluprost, etc.), combinations of GGA and a prostamide drug (GGA and bimatoprost, etc.), and combinations of GGA and a prostone drug (GGA and isopropyl unoprostone); combinations of GGA and a sympatholytic agent such as, combinations of GGA and a β-blocker (GGA and timolol maleate, GGA and gel-forming timolol, GGA and carteolol hydrochloride, GGA and gel-forming carteolol, etc.), combinations of GGA and a β1-blocker (GGA and betaxolol hydrochloride, etc.), combinations of GGA and an αβ-blocker (GGA and levobunolol hydrochloride, GGA and nipradilol, GGA and bunazosin hydrochloride, etc.), and combinations of GGA and an α2-blocker (GGA and brimonidine tartrate); combinations of GGA and a parasympathomimetic drug, such as GGA and pilocarpine hydrochloride, and GGA and distigmine bromide; combinations of GGA and a sympathomimetic drug, such as GGA and epinephrine, GGA and epinephrine bitartrate, and GGA and dipivefrin hydrochloride; combinations of GGA and a carbonic anhydrase inhibitor, such as GGA and dorzolamide hydrochloride, and GGA and brinzolamide; combinations of GGA and a specific inhibitor to ROCK (Rho-associated coiled coil forming protein kinase), such as GGA and SNJ-1656, and GGA and K-115; combinations of GGA and a calcium antagonist, such as GGA and lomerizine hydrochloride; combinations of GGA and an EP2 agonist, such as GGA and DE-117; combinations of GGA and an adenosine A2a receptor agonist, such as GGA and OPA-6566; combinations of GGA and a therapeutic agent for age-related macular degeneration, such as combinations of GGA and a VEGF aptamer (GGA and pegaptanib sodium) and combinations of GGA and a VEGF inhibitor (GGA and ranibizumab, and GGA and bevacizumab).

Among these, preferred are combinations of GGA and a prostaglandin F2α derivative and combinations of GGA and a sympatholytic drug (especially preferred are combinations of GGA and a β-blocker) because these combinations exhibit a very high prophylactic, ameliorating or therapeutic effect for a retinal disease.

The inhalant can comprise a pharmacologically or physiologically active component other than the prophylactic, ameliorating or therapeutic component for a retinal disease. Examples of the pharmacologically or physiologically active component include decongestants, drugs for restoring extraocular muscle function, anti-inflammatory drugs or astringent drugs, antihistaminics or antiallergics, vitamins, amino acids, antibacterial drugs or bactericides, etc.

The GGA content of the inhalant is preferably 0.001% by weight or more, more preferably 0.01% by weight or more, further more preferably 0.1% by weight or more, relative to the total amount of the preparation. The GGA content is preferably 80% by weight or less, more preferably 60% by weight or less, further more preferably 50% by weight or less. GGA in the above ranges is sufficient to exhibit the prophylactic, ameliorating or therapeutic effect for a retinal disease.

The GGA content of the inhalant is, for example, about 0.001 to 80% by weight, about 0.001 to 60% by weight, about 0.001 to 50% by weight, about 0.01 to 80% by weight, about 0.01 to 60% by weight, about 0.01 to 50% by weight, about 0.1 to 80% by weight, about 0.1 to 60% by weight, or about 0.1 to 50% by weight, relative to the total amount of the preparation.

In the inhalant, the additives and the pharmacologically or physiologically active components other than GGA can be used alone or in combination of two or more thereof.

Kit

The agent of the present invention may be a kit comprising separate compositions: a composition comprising GGA and a composition comprising a pharmacologically or physiologically active component other than GGA; or may be a composition comprising all the components in a single dosage form. The agent of the present invention may also be a kit comprising separate compositions: a composition comprising GGA and a composition comprising a particular additive. In a kit, compositions may be separately packed into different containers, or may be packed into a container that allows mixing at the time of use (compositions to be prepared at the time of use). In a kit, any number (e.g., two, three, etc.) of dosage forms may be contained.

When the agent of the present invention is a kit comprising separate compositions: a composition comprising GGA and a composition comprising another component (including the above cases of a kit comprising compositions separately packed into different containers and a kit comprising compositions to be prepared at the time of use), the GGA content described above for each type of preparation is the percentage relative to the total amount of the mixed compositions.

Target Diseases

A target retinal disease of the present invention may be any retinal disease as long as it is a disease involving the degeneration, impairment or destruction of a constituent cell of the retina, or a disease resulting from the degeneration, impairment or destruction of a constituent cell of the retina. Examples of these diseases include glaucoma, retinitis pigmentosa, age-related macular degeneration, diabetic retinopathy, retinal detachment, diabetic maculopathy, hypertensive retinopathy, retinal vascular occlusion (retinal artery occlusion; retinal vein occlusion such as central retinal vein occlusion and branch retinal vein occlusion; etc.), retinal arteriosclerosis, retinal tear, retinal hole, macular hole, ophthalmorrhagia, posterior vitreous detachment, pigmented paravenous retinochoroidal atrophy, gyrate atrophy of the retina and choroid, choroideremia, crystalline retinopathy, retinitis punctata albescens, corneal dystrophy, cone dystrophy, central areolar choroidal dystrophy, Doyne's honeycomb retinal dystrophy, vitelliform macular dystrophy, cystoid macular edema, occult macular dystrophy, Stargardt disease, retinoschisis, central serous chorioretinopathy (central retinopathy), spinocerebellar ataxia type 7, familial exudative vitreoretinopathy, enhanced S-cone syndrome, angioid streaks, autosomal dominant optic atrophy, autosomal dominant drusen, familial drusen, acute zonal occult outer retinopathy, cancer-associated retinopathy, light damage, ischemic retinopathy, inflammation-induced retinal degenerative disease, etc.

Among these, more suitable target diseases are glaucoma, retinitis pigmentosa, age-related macular degeneration, and diabetic retinopathy, and furthermore suitable target disease is glaucoma.

The target disease of the present invention also includes a disease involving the impairment of any constituent cell of the retina, and a disease resulting from the impairment of any constituent cell of the retina. Examples of the constituent cells of the retina include retinal ganglion cells, amacrine cells, horizontal cells, Muller glial cells, bipolar cells, retinal visual cells (cones and rods), retinal pigment epithelial cells, etc. Especially suitable target is a disease involving or resulting from the impairment of retinal ganglion cells or retinal pigment epithelial cells.

The target disease of the present invention also includes a disease involving or resulting from the impairment of any of the constituent layers of the retina, i.e., the inner limiting membrane, the nerve fiber layer, the ganglion cell layer, the inner plexiform membrane, the inner nuclear layer, the outer plexiform layer, the outer nuclear layer, the external limiting membrane, the visual cell layer, and the retinal pigment epithelium layer. Particularly suitable target is a disease involving or resulting from the impairment of the ganglion cell layer, the inner nuclear layer, or the outer nuclear layer.

The target patient to whom the present invention is suitably applied is a patient with the above retinal disease.

As described above, GGA contained in the agent of the present invention protects a retinal cell, i.e., promotes the survival of a retinal cell or inhibiting the degeneration, impairment or destruction of a retinal cell, thereby preventing, ameliorating or treating a retinal disease.

Therefore, the present invention encompasses a protective agent for a retinal cell, a promoting agent for the survival of a retinal cell, or a suppressing agent for the degeneration, impairment or destruction of a retinal cell, these agent comprising, as an active ingredient, GGA which (a) is a mixture of the all-trans form and the mono-cis form (in particular the 5Z-mono-cis form), the all-trans form content of the mixture being 80% by weight or more, (b) consists of the all-trans form, (c) consists of the 5Z-mono-cis form, or (d) is a mixture of the all-trans form and the mono-cis form (in particular the 5Z-mono-cis form), the mono-cis form content of the mixture being very high.

Particularly suitable target retinal cells of these agents are as described above. The components, dose, properties, dosage form, etc. of the preparations are as described for the prophylactic, ameliorating or therapeutic agent for a retinal disease of the present invention.

In the present invention, the term "prophylactic" is understood to include preventing or delaying the onset of a disease and reducing the incidence, and the term "ameliorating" and "therapeutic" are understood to include reducing the symptoms, suppressing the progress of the symptoms, and leading to remission or cure.

Usage

<Ophthalmic Preparation>

When the agent of the present invention is an eye drop, the eye drop comprising GGA in the above concentration ranges is instilled, for example, about 1 to 5 times a day, preferably about 1 to 3 times a day, in an amount of about 1 to 2 drops each time.

When the agent of the present invention is an eye wash, eye washing is performed, for example, about 1 to 10 times a day, preferably about 1 to 5 times a day, each time using about 1 to 20 mL of the eye wash comprising GGA in the above concentration ranges.

When the agent of the present invention is an ophthalmic ointment, the ophthalmic ointment comprising GGA in the above concentration ranges is applied to the eye, for example, about 1 to 5 times a day, preferably about 1 to 3 times a day, in an amount of about 0.001 to 5 g each time.

When the agent of the present invention is an intraocular injection, the intraocular injection comprising GGA in the above concentration ranges is injected, for example, about 1 to 3 times per day to 14 days, preferably once per day to 14 days, in an amount of about 0.005 to 1 mL each time.

When the agent of the present invention is a contact lens solution (a washing solution, a storage solution, a sterilizing solution, a multipurpose solution, package solution, etc.), a preservative for a harvested ocular tissue (a cornea etc.) for transplantation, or an irrigating solution for surgery, such a composition comprising GGA in the above concentration ranges is used in a usual dosage and regimen of such a type of preparation.

When the agent of the present invention is a sustained-release contact lens preparation, the contact lens comprising GGA in the above amount is replaced with a fresh one, for example, about 1 to 3 times per day to 14 days, preferably once per day to 14 days.

When the agent of the present invention is a sustained-release intraocular implant, about 1 to 14 days after the implantation of the implant comprising GGA in the above amount, a fresh one is implanted as needed.

When the agent of the present invention is an ophthalmic composition, the daily dosage of GGA is preferably 50 ng or more, more preferably 500 ng or more, further more preferably 5 µg or more. The daily dosage of GGA is preferably 50 mg or less, more preferably 20 mg or less, further more preferably 10 mg or less.

When the agent of the present invention is an ophthalmic composition, the daily dosage of GGA is, for example, about 50 ng to 50 mg, about 50 ng to 20 mg, about 50 ng to 10 mg, about 500 ng to 50 mg, about 500 ng to 20 mg, about 500 ng to 10 mg, about 5 µg to 50 mg, about 5 µg to 20 mg, or about 5 µg to 10 mg.

<Other Preparations>

When the agent of the present invention is in a dosage form other than an ophthalmic preparation, the daily dosage of GGA is preferably about 0.1 mg or more, more preferably about 1 mg or more, further more preferably about 5 mg or more. The daily dosage of GGA is preferably about 5000 mg or less, more preferably about 1000 mg or less, further more preferably about 500 mg or less.

When the agent of the present invention is in a dosage form other than an ophthalmic preparation, the daily dosage of GGA is, for example, preferably about 0.1 to 5000 mg, more preferably about 1 to 1000 mg, further more preferably about 5 to 500 mg. The daily dosage is divided into, for example, about 1 to 5 administrations, preferably about 1 to 3 administrations.

The administration period varies depending on the type and stage of the disease, the age, weight, and sex of the patient, the route of administration, etc., and can be selected as appropriate, for example, from the range from about one day to 30 years. For example, when the patient has a retinal disease such as glaucoma, retinitis pigmentosa, age-related macular degeneration and diabetic retinopathy, the retinal disease may be prevented for, ameliorated in or cured in an administration period of about 1 to 20 years, especially as short as 1 to 10 years. When the retinal protective action exhibited by the ophthalmic composition of the present invention suppresses the progress of a retinal disease, the administration can be further continued.

The present invention includes (i) a method for preventing, ameliorating or treating a retinal disease, the method comprising the step of administering to a patient with a retinal disease an effective amount of the GGA described in the following (a), (b), (c) or (d), thereby preventing, ameliorating or treating the retinal disease, (ii) a method for suppressing the degeneration, impairment or destruction of a retinal cell, the method comprising the step of administering to a patient with a retinal disease an effective amount of the GGA described in the following (a), (b), (c) or (d), thereby suppressing the degeneration, impairment or destruction of a retinal cell, and (iii) a method for protecting a retinal cell, the method comprising the step of administering to a patient with a retinal disease an effective amount of the GGA described in the following (a), (b), (c) or (d), thereby protecting a retinal cell:

(a) a mixture of the all-trans form and the mono-cis form (in particular the 5Z-mono-cis form), the all-trans form content of the mixture being 80% by weight or more, (b) GGA consisting of the all-trans form, (c) GGA consisting of the 5Z-mono-cis form, or (d) a mixture of the all-trans form and the mono-cis form (in particular the 5Z-mono-cis form), the mono-cis form content of the mixture being very high.

GGA is administered in any of the preparation forms of the present invention described above. The administration method varies depending on the dosage forms and examples of the administration method include ocular instillation, eye washing, application to the eye, spray to the eye, implantation to the eye, wearing a contact lens, injection (injection into the eye, for example, injection into the vitreous body etc., intravenous injection, hypodermic injection, intramuscular injection), oral administration, transdermal administration, insertion into the rectum, inhalation, etc. In the case of the ophthalmic agent, the agent is administered to the eye.

The target disease, the target patient and the type of retinal cells to be targeted are as described for the agent of the present invention.

EXAMPLES

The present invention will be described in more detail below with reference to Examples, but the present invention is not limited thereto.

(1) Preparation of Geranylgeranylacetone

Marketed teprenone (all-trans form:5Z-mono-cis form=3:2 (weight ratio)) (Wako Pure Chemical Industries, Ltd.) was purchased and the all-trans form was separated and purified by silica gel chromatography.

The above preparative purification was carried out using silica gel (PSQ60B, Fuji Silysia Chemical Ltd.) filled in a glass tube and a mobile phase of n-hexane/ethyl acetate (9:1). After the separation, each fraction was concentrated and dried under reduced pressure and the degree of purification and structure of the all-trans form were determined by GC and $^1$H-NMR (solvent: deuterated chloroform; internal standard: tetramethylsilane) (about 20% yield).

<GC Measurement Conditions>

Column: DB-1 (J&W Scientific, 0.53 mm×30 m, film thickness of 1.5 µm)

Column temperature: elevated at a rate of 5° C./minute from 200° C. to 300° C. (10 minutes)

Vaporizing chamber temperature: 280° C.

Detector temperature: 280° C.

Carrier gas: helium

Hydrogen pressure: 60 kPa

Air pressure: 50 kPa

Makeup gas pressure: 75 kPa (nitrogen gas)

Total flow: 41 mL/min

Column flow: 6.52 mL/min
Linear velocity: 58.3 cm/sec
Split ratio: 5:1
Injection volume: 1 μL of 0.1 g/100 mL sample (in ethanol)

The marketed teprenone and the all-trans form purified as described above were mixed at various ratios to give GGAs at desired weight ratios (all-trans form:5Z-mono-cis form=7:3, 8:2, 9:1, etc. (weight ratio)). Since the stability of the mixtures was unknown, the mixtures were prepared at the time of use.

(2) Evaluation of Protective Effect for Retinal Neuronal Cells Against Ischemic Cell Death Induced by Hypoxia and Low Glucose The progress of visual impairment in glaucoma is associated with retinal ganglion cell (RGC) death due to blood flow failure occurring near the optic nerve (Folia Pharmacol. Jpn. 128, 255-258 (2006)). With the use of PC12, which is a typical neural cell line established from rat adrenal cortex pheochromocytoma and used also as a model cell for the functional evaluation of RGC (J Neurosci Res. 2000 May 15; 60(4): 495-503), the cytoprotective effect of GGA against ischemic cell death induced by hypoxia and low glucose was evaluated.

<Evaluation Method>

Test samples were prepared as follows. The test substances were four types of GGAs that contain the all-trans form and the 5Z-mono-cis form at a weight ratio of 10:0, 8:2, 6:4, and 0:10, respectively. An amount of 100 mg of each GGA and 0.25 mg of DL-α-tocopherol acetate (Wako Pure Chemical Industries) as an antioxidant were weighed out and dissolved in 789 mg of 100% ethanol. A base was prepared in the same manner as described above except that GGA was not used. Each of the GGAs having a weight ratio of 10:0, 8:2, and 6:4 dissolved in 789 mg of 100% ethanol was diluted with a high-glucose (4.5 g/L) Dulbecco's modified Eagle's basal medium (DMEM) supplemented with 10% (v/v) horse serum (DS Pharma Biomedical) and 5% (v/v) fetal calf serum (Daiichi Pure Chemicals) to a concentration adjusted so that the all-trans form content was substantially 30 μM. The GGA having a weight ratio of 0:10 containing only the 5Z-mono-cis form was also diluted so that the concentration was 30 μM. The base was diluted by the same dilution factor as that for the GGA having a weight ratio of the all-trans form:the 5Z-mono-cis form of 6:4.

PC12 (purchased from DS Pharma Biomedical) was seeded onto a collagen IV coated 96-well microplate (IWAKI) at $2.0 \times 10^4$ cells/100 μL per well and incubated in the DMEM described above under 5% $CO_2$ at 37° C. for 48 hours.

After 48 hours of incubation, the supernatant of the cell culture was removed and replaced with the previously prepared DMEMs containing the GGAs and incubation was performed under 5% $CO_2$ at 37° C. for 2 hours. After 2 hours of incubation, the medium was replaced with a low-glucose (1.0 g/L) DMEM supplemented with 2% horse serum and 1% fetal calf serum, the oxygen condition was changed to zero percent $O_2$ using Anaeropack 5% (Mitsubishi Gas Chemical), and incubation was performed under 5% $CO_2$ and the low oxygen condition at 37° C. for 8 hours. For a non-treated group, incubation was performed in a high-glucose (4.5 g/L) DMEM supplemented with 2% (v/v) horse serum and 1% (v/v) fetal calf serum under 5% $CO_2$ and normal oxygen concentration at 37° C. for 8 hours.

<Test Results>

After 8 hours of incubation, 100 μL of an equivalent mixture of a cell viability detection reagent Cell Titer-Glo (Promega) and PBS was added to each well and the luminescence produced by the reaction with ATP in living cells was measured with a luminometer (GloMax; Promega). The cell viability was calculated from the measured luminescence by the following formula and the cytoprotective effect of GGA against oxidative stress by hydrogen peroxide was examined.

Cell viability(%)=100×[(luminescence of base- or GGA-treated group)/(luminescence of non-treated group)]

The results are shown in FIG. 1. As is apparent from FIG. 1, the GGA-treated groups showed significantly higher cell viabilities at all weight ratios than that of the base-treated group. The GGAs having a weight ratio of the all-trans form:the 5Z-mono-cis form of 10:0, 8:2, and 0:10 showed significantly higher cytoprotective effects than that of the GGA having a weight ratio of 6:4. (n=10, *: P<0.05, **: P<0.01, by Tukey-Kramer test. No significant difference was observed among 8:2, 10:0, and 0:10.)

(3) Evaluation of Neurite Outgrowth Inducing Effect Using Culture System of Rat-Derived Retinal Ganglion Cells (RGC)

The progress of visual impairment in glaucoma is associated with retinal ganglion cell (RGC) death due to blood flow failure occurring near the optic nerve (Folia Pharmacol. Jpn. 128, 255-258 (2006)). Accordingly, a culture system of rat-derived retinal neurons (Current protocols in Neuroscience 3.22.1-3.22.10, October 2010), which is widely used as one of study tools for optic nerve diseases such as a glaucoma, was used to examine the neurite outgrowth inducing effect of GGA.

<Evaluation Method>

Four-day-old Wistar rats (Japan SLC, Inc.) were euthanized by cervical dislocation and the eyeballs were harvested. The harvested eyeballs were immersed in 70% ethanol for 10 seconds and transferred to a Hanks' balanced salt solution containing 100 U/mL penicillin and 100 μg/mL streptomycin. Under a stereoscopic microscope, the corneas, irises, crystalline lenses, and vitreous bodies were removed using scissors for surgery and forceps, and the retinal tissue was harvested. The harvested retinal tissue was transferred to a centrifugation tube containing 5 mL of a basal medium for neuronal cells (Neurobasal, Invitrogen) containing 100 U/mL penicillin, 100 μg/mL streptomycin, a neural cell culture supplement (B27™-Supplement, Invitrogen), 1 μM L-cysteine (Kyowa Hakko Bio) and 15 U/mL papain (Sigma Aldrich) and incubated at 37° C. for 30 minutes. Thirty minutes later, the supernatant was removed and the tissue was washed twice with Neurobasal containing 100 U/mL penicillin, 100 μg/mL streptomycin, and B27™-Supplement. After washing, 2 mL of Neurobasal was added, the tissue was divided into small cell masses by pipetting with a dry-heat sterilized Pasteur pipette (Hilgenberg), and transferred to 50 mL of Neurobasal that was prepared in advance. After centrifugation at 900×g for 5 minutes, the supernatant was removed, and the residue was suspended again in 6 mL of Neurobasal to give a cell suspension. The cell suspension was filtered through a 40 μm nylon mesh cell strainer (Japan BD) for removal of aggregated cell masses. The obtained cells were seeded onto a poly-D-lysine/laminin coated 6-well plate (Japan BD) and incubated under 5% $CO_2$ at 37° C.

The test substances were two types of GGAs: GGA consists of the all-trans form, and GGA contains the all-trans form and the 5Z-mono-cis form at a weight ratio of 6:4. An amount of 100 mg of each GGA and 0.25 mg of DL-α-tocopherol acetate (Wako Pure Chemical Industries) as an antioxidant were weighed out and dissolved in 789 mg of 100% ethanol. A base was prepared in the same manner as described above except that GGA was not used. The concentration of each of the GGAs having a weight ratio of 10:0 and 6:4 dissolved in 789 mg of 100% ethanol was adjusted so that the all-trans form content was substantially 3 µM. The base was diluted by the same dilution factor as that for the GGA of 6:4. Each of the GGAs and the base were then added to the cell culture supernatant 2 hours after cell seeding and incubation was performed under 5% $CO_2$ at 37° C. for 48 hours.

<Results>

After 48 hours of incubation, the cell culture supernatant was removed and the cells were fixed with a 4% paraformaldehyde phosphate buffer solution (Wako Pure Chemical Industries) and 100% methanol (Wako Pure Chemical Industries) at room temperature for 30 minutes. The cells were washed with phosphate buffer (PBS) (Kohjin Bio) and blocking was performed with PBS containing 2% (w/v) bovine serum albumin (Sigma Aldrich) and 0.05% (v/v) Tween 20 (Sigma Aldrich) at room temperature for 30 minutes. Thirty minutes later, 1 mL of βIII tubulin antibody (Promega) diluted to 1000-fold in PBS was added to each well and incubation was performed at room temperature for 2 hours. Two hours later, the diluted antibody solution was removed and washing with PBS was performed 3 times. Then, 1 mL of Alexa Fluor 488 goat anti-mouse antibody (Invitrogen) diluted to 1000-fold in PBS was added to each well and incubation was performed at room temperature for 1 hour. One hour later, the diluted antibody solution was removed, washing with PBS was performed 3 times, and 3 mL of PBS was added to each well. With the use of an imaging cytometer (In Cell Analyzer 1000, GE Healthcare Bioscience), examination was performed at arbitrarily selected 4 locations in each well (excitation wavelength: 475 nm; fluorescence wavelength: 535 nm), and the mean of the length (µm) of the fluorescence stained neurites of RGC was calculated.

Figure 2:
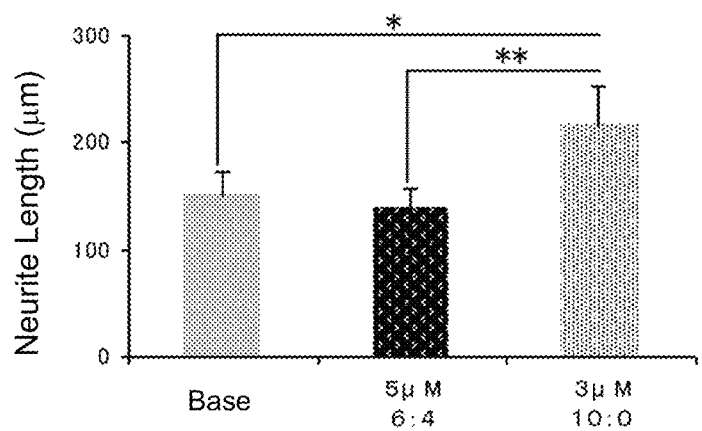
FIG. 2 shows the neurite outgrowth inducing effect of GGA in rat RGC.

The results are shown in FIG. 2. As is apparent from FIG. 2, the group treated with GGA having a weight ratio of the all-trans form:the 5Z-mono-cis form of 10:0 showed a significant neurite inducing effect as compared with the group treated with GGA having a weight ratio of the all-trans form:the 5Z-mono-cis form of 6:4 and the base-treated group (n=4, *: P<0.05, **: P<0.01, by Tukey-Kramer test).

Figure 3:
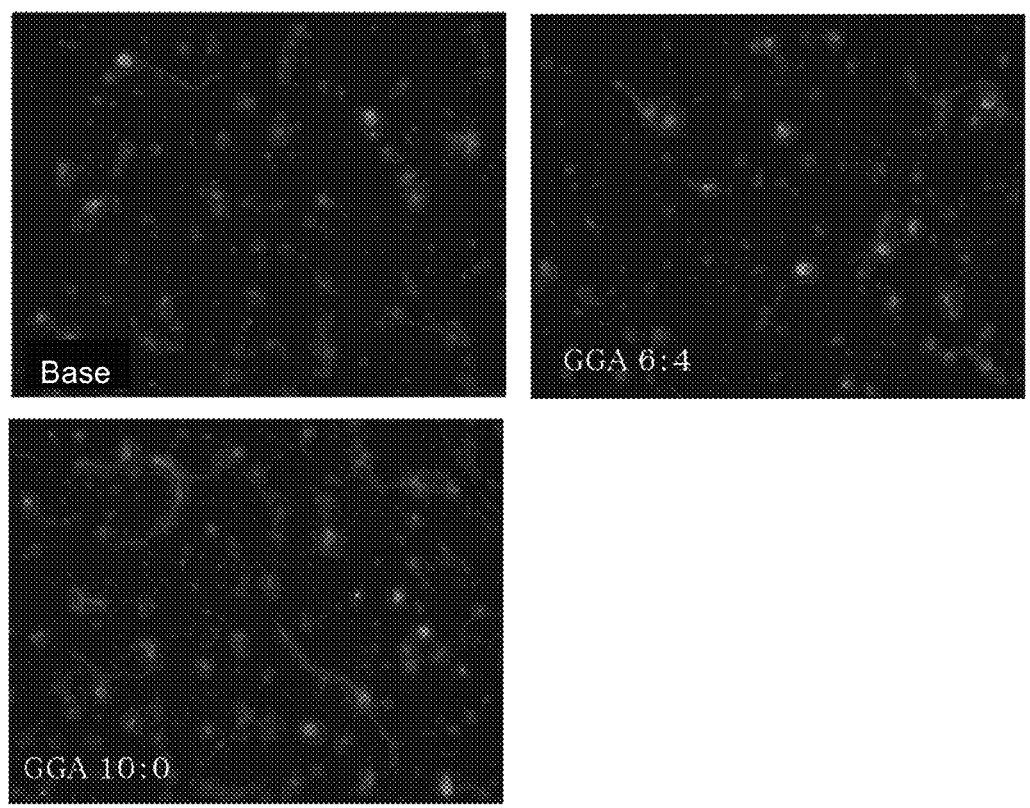
FIG. 3 is photographs showing the neurite outgrowth inducing effect of GGA in rat RGC.

Typical observation images of the fluorescence stained rat RGC are shown in FIG. 3. As is apparent form the images, the group treated with GGA of 10:0 showed a significant neurite inducing effect as compared with the group treated with GGA of 6:4.

(4) Evaluation of Protective Effect for Retinal Pigment Epithelial Cells Against Oxidative Stress by Hydrogen Peroxide The involvement of oxidative stress in ophthalmologic diseases has been widely reported. Such involvement has been observed in, in addition to glaucoma and cataract, retinal diseases such as retinal diseases due to diabetes, hypertension, hyperlipemia, etc., age-related macular degeneration, retinopathy of prematurity, retinal vascular occlusion, retinal light damage, etc. (Nippon Ganka Gakkai Zasshi. 112, 22-29 (2008)). In the retina, the retinal pigment epithelium exists in an environment in which reactive oxygen easily generates (Invest Opthalmol V is Sci. 2006 July 47(7): 3164-3177). The cytoprotective effect of GGA against oxidative stress by hydrogen peroxide was examined using a human-derived retinal pigment epithelial cell line, ARPE-19.

<Evaluation Method>

The test substances were three types of GGAs that contain the all-trans form and the 5Z-mono-cis form at a weight ratio of 10:0, 8:2, and 6:4, respectively, and with the use of these test substances, test solutions were prepared as follows. An amount of 100 mg of each GGA and 0.25 mg of DL-α-tocopherol acetate (Wako Pure Chemical Industries) as an antioxidant were weighed out and dissolved in 789 mg of 100% ethanol. A base was prepared in the same manner as described above except that GGA was not used. Each of the GGAs having a weight ratio of 10:0, 8:2, and 6:4 dissolved in 100% ethanol was diluted with a Dulbecco's modified Eagle's basal medium/Ham's-F12 mixed liquid medium (1:1) (DMEM/F-12, Invitrogen) supplemented with 10% (v/v) fetal calf serum (Daiichi Pure Chemicals) to a concentration adjusted so that the all-trans form content was substantially 280 µM. The base was diluted by the same dilution factor as that for the GGA of 6:4. The above diluted solutions were used as test solutions.

ARPE-19 (purchased from ATCC) was seeded onto a 96-well microplate (CORNING) at $1.5 \times 10^4$ cells/100 µL per well and incubated in the DMEM/F-12 described above under 5% $CO_2$ at 37° C. for 48 hours.

After 48 hours of incubation, the supernatant of the cell culture was removed and replaced with the previously prepared test solutions and incubation was performed under 5% $CO_2$ at 37° C. for 14 hours. Immediately before the end of the incubation, a DMEM/F-12 supplemented with 750 µM hydrogen peroxide was prepared by adding hydrogen peroxide for precision analysis (Wako Pure Chemical Industries) to a DMEM/F-12. After 14 hours of incubation, the cell culture supernatant was removed and 200 µL of phosphate buffer (PBS, Kohjin Bio) was added to each well. PBS was promptly removed and replaced with the previously prepared DMEM/F-12 supplemented with hydrogen peroxide, and incubation was performed under 5% $CO_2$ at 37° C. for 2 hours. For a non-treated group, PBS was replaced with a DMEM/F-12 not containing hydrogen peroxide.

<Results>

After 2 hours of incubation, the cell culture supernatant was removed, and 200 µL of PBS was added to each well and promptly removed. Then, 100 µL of an equivalent mixture of a cell viability detection reagent Cell Titer-Glo (Promega) and PBS was added to each well and the luminescence produced by the reaction with ATP in living cells was measured with a luminometer (GloMax; Promega). The cell viability was calculated from the measured luminescence by the following formula and the cytoprotective effect of GGA against oxidative stress by hydrogen peroxide was examined.

Cell viability(%)=100×[(luminescence of base- or GGA-treated group)/(luminescence of non-treated group)]

Figure 4:
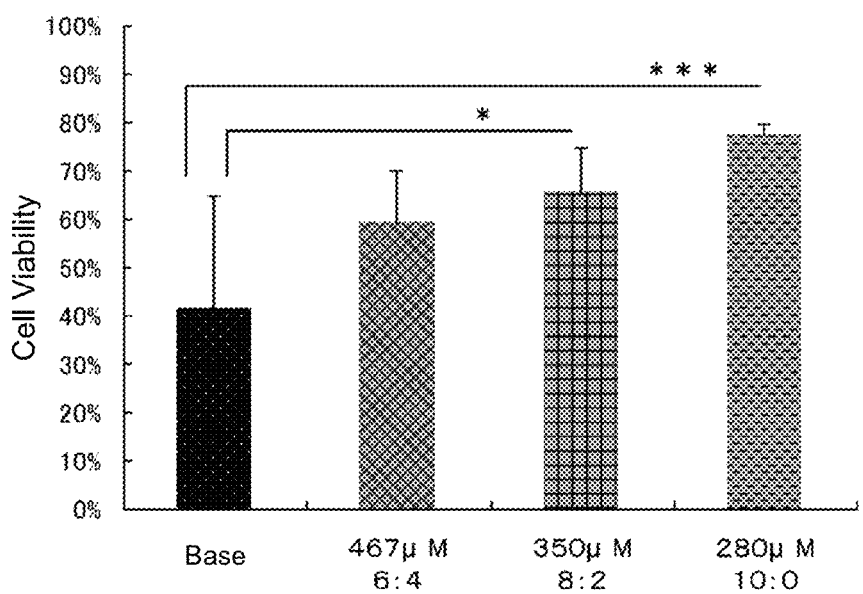
FIG. 4 shows the cytoprotective action of GGA against oxidative stress.

The results are shown in FIG. 4. As is apparent from FIG. 4, the GGA-treated groups showed higher cell viabilities at all weight ratios than that of the base-treated group. The GGAs of 10:0 and 8:2 showed significantly higher cell viabilities than that of the base-treated group (n=3, *: P<0.05, ***: P<0.001, by Tukey-Kramer test).

(5) Evaluation of Inhibitory Effect on IL-8 Production from Retinal Pigment Epithelial Cells Age-related macular degeneration is known to involve the accumulation of drusen under the retinal pigment epithelium. Drusen attract macrophages and macrophages secrete TNF-α. TNF-α acts on the retinal pigment epithelium and its peripheral tissue, and the cells subsequently produce a variety of cytokines and cause inflammation (Mol Vis. 2008 14: 2292-303). Atypical cytokine that is involved in neutrophil migration and spreads inflammation is interleukin-8 (IL-8). In this experiment, the inhibitory effect of GGA on IL-8 production by TNF-α was examined using a human-derived retinal pigment epithelial cell line, ARPE-19.

<Evaluation Method>

The test substances were two types of GGAs: GGA consists of the all-trans form, and GGA contains the all-trans form and the 5Z-mono-cis form at a weight ratio of 6:4. With the use of these test substances, test solutions were prepared as follows. An amount of 100 mg of each GGA and 0.25 mg of DL-α-tocopherol acetate as an antioxidant were weighed out and dissolved in 789 mg of 100% ethanol. A base was prepared in the same manner as described above except that GGA was not used. Each of the GGAs, which were the GGA consisting of the all-trans form and the GGA containing the all-trans form and the 5Z-mono-cis form at a weight ratio of 6:4, dissolved in 789 mg of 100% ethanol was diluted with a DMEM/F-12 to a concentration adjusted so that the all-trans form content was substantially 50 μM. The base was diluted by the same dilution factor as that for the GGA having a weight ratio of the all-trans form:the 5Z-mono-cis form of 6:4. The above diluted solutions were used as test solutions.

ARPE-19 was seeded onto a 96-well microplate (CORNING) at $2.5 \times 10^4$ cells/100 μL per well and incubated in a DMEM/F-12 supplemented with 10% (v/v) fetal calf serum under 5% $CO_2$ at 37° C. for 24 hours.

After 24 hours of incubation, the supernatant of the cell culture was removed, 200 μL of each of the previously prepared test solutions was added to each well, and incubation was performed under 5% $CO_2$ at 37° C. for 16 hours. For a non-treated group, a DMEM/F-12 was added in the same manner as described above and incubation was performed. Immediately before the end of the incubation, recombinant human TNF-α (R&D Systems) was prepared in a DMEM/F-12 to a concentration of 10 ng/mL. After 16 hours of incubation, 2 μL of the previously prepared DMEM/F-12 supplemented with TNF-α was added to the test solution in each well, and incubation was performed under 5% $CO_2$ at 37° C. for 4 hours. The non-treated group was incubated in the same manner except that TNF-α was not added thereto.

<Results>

After 4 hours of incubation, 150 μL of the cell culture supernatant was collected and stored at −80° C. The rest of the cell culture supernatant was removed, and 200 μL of PBS was added to each well and promptly removed. Then, 100 μL of an equivalent mixture of a cell viability detection reagent Cell Titer-Glo and PBS was added to each well and the luminescence produced by the reaction with ATP in living cells was measured with a luminometer. From the measured luminescence, the cell viability was calculated by the following formula.

Cell viability(%)=100×[(luminescence of GGA-treated group)/(luminescence of base-treated group)]

The stored cell culture supernatant was allowed to warm to room temperature, and the IL-8 concentration was quantified with Human CXCL8/IL-8 Quantikine ELISA Kit (R&D Systems). The procedure was performed in accordance with the instruction manual attached to the kit and the measured absorbance was corrected by dividing it by the cell viability. The measurement of the absorbance was performed using a microplate reader (VersaMax, Molecular Devices) at a measurement wavelength of 450 nm and a correction wavelength of 540 nm (temperature in the chamber: 20 to 25° C.). The IL-8 concentration of each treatment group was obtained by calculating an IL-8 concentration corresponding to the corrected measured value and subtracting, from it, the IL-8 concentration of the non-treated group as a background.

Figure 5:
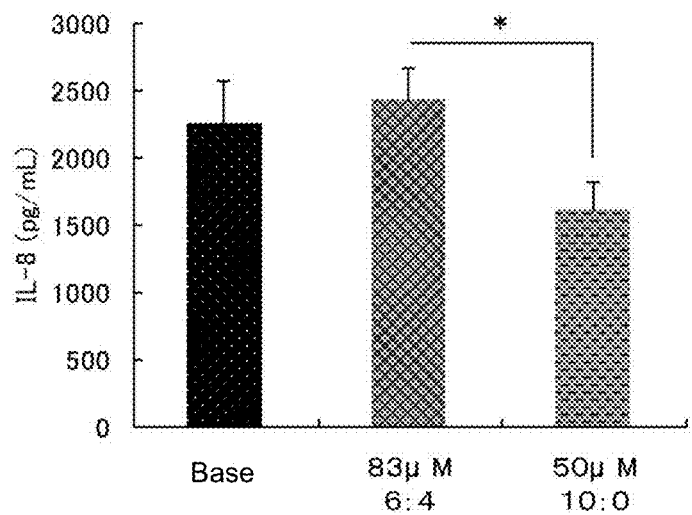
FIG. 5 shows the reducing effect of GGA on IL-8 production by TNF-α.

The results are shown in FIG. 5. As is apparent from FIG. 5, the group treated with GGA having a weight ratio of the all-trans form:the 5Z-mono-cis form of 10:0 (the all-trans form only) showed a significant inhibitory effect on IL-8 production as compared with the group treated with GGA having a weight ratio of the all-trans form:the 5Z-mono-cis form of 6:4 (n=3, *: P<0.05, by Tukey-Kramer test).

(6) Evaluation of Protective Effect for Retinal Ganglion Cells Against Nerve Damage Inducing Action of NMDA In recent years the glutamate analogue NMDA (N-methyl-D-aspartate) has been widely reported to be one of causative agents of neurodegenerative diseases including Alzheimer's disease. In the ophthalmic field, NMDA is considered to be involved in optic nerve damage in glaucoma (Brain Research Bulletin, 81 (2010) 349-358). Accordingly, in this experiment rat models with glaucoma induced by NMDA were used to evaluate the neuroprotective effect of GGA.

Evaluation Method

To Sprague-Dawley (SD) rats, the all-trans form, the 5Z-mono-cis form and teprenone were separately pre-administered by oral administration (Test Example 1), intravitreal administration (Test Example 2) or ocular instillation administration (Test Example 3) and 5 μL of NMDA was administered into the vitreous body to induce nerve damage. For Test Example 2, a marketed therapeutic eye drop for glaucoma, AIPHAGAN (trade name), was intravitreally administered as a positive control once a day for five days. For each of Test Examples, a base not containing GGA or AIPHAGAN was administered as a control in the same manner as described above.

The dosage and regimen of Test Examples 1 to 3 are shown in Table 1 and the constitution of the base used in each tests are shown in Table 2.

TABLE 1

| | | Pre-administration (GGA) | | | Damage induction |
|---|---|---|---|---|---|
| | Route of administration | Administered concentration | Administration period | Frequency of administration per day | (NMDA) Administered concentration |
| Test Example 1 | Oral | 800 mg/kg | 2 days | 1 | 4 mM |

TABLE 1-continued

|  | Pre-administration (GGA) | | | | Damage induction |
|---|---|---|---|---|---|
|  | Route of administration | Administered concentration | Administration period | Frequency of administration per day | (NMDA) Administered concentration |
| Test Example 2 | Intravitreal | 0.05% w/v | 5 days | 1 | 40 mM |
| Test Example 3 | Ocular instillation | 1% w/v | 5 days | 5 | 4 mM |

TABLE 2

| g/100 mL | Test Example 1 | Test Example 2 | Test Example 3 |
|---|---|---|---|
| Gum arabic | 5.000 | — | — |
| α-tocopherol | 0.200 | — | — |
| Boric acid | — | 1.300 | 1.300 |
| Borax | — | 0.400 | 0.400 |
| Polysorbate 80 | — | 2.000 | 2.000 |
| POE hydrogenated castor oil 60 | — | 2.000 | 2.000 |
| POE castor oil | — | 0.100 | 0.100 |
| Dibutylhydroxytoluene | — | 0.005 | 0.005 |
| Purified water | q.s. | q.s. | q.s. |

Three days after administration of NMDA, the eyeballs were harvested, fixed with half Karnovsky's fixative for 24 hours, embedded in paraffin, thin sectioned and stained with hematoxylin-eosin (HE) to prepare histopathological sections. The histological sections were observed under an optical microscope and the thickness (μm) of the inner plexiform layer (IPL) of the retina was measured. From the thickness of the inner plexiform layer (IPL) of the retina, the neuroprotective effects of the test preparations were evaluated.

Results

Figure 6:
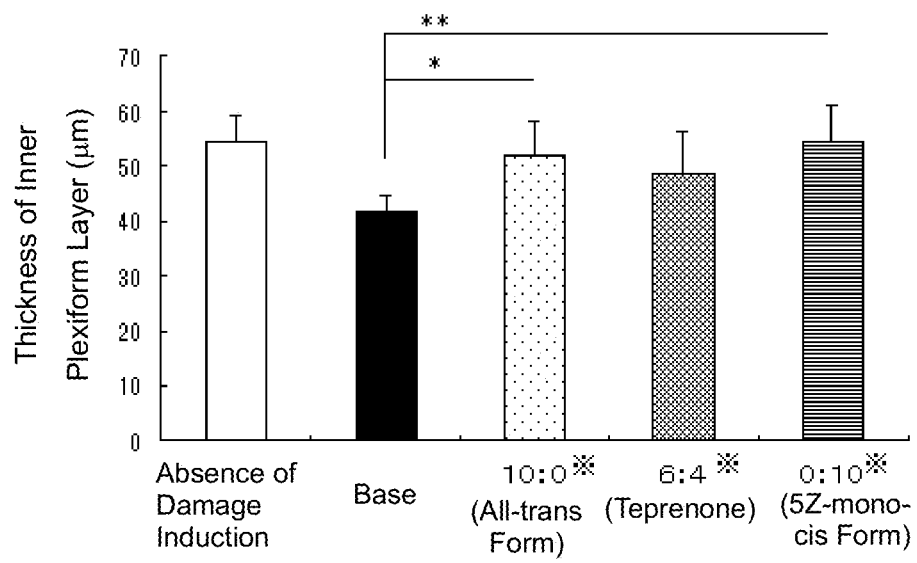
FIG. 6 shows the ocular neuroprotective actions of the all-trans form and the 5Z-mono-cis form in rat models with glaucoma induced by NMDA.

The results of Test Example 1 are shown in FIG. 6. As is apparent from FIG. 6, in the case of oral administration, the all-trans form and the 5Z-mono-cis form showed significant neuroprotective effects against nerve damage by NMDA as compared with the base (*p<0.05, **<0.01, by Dunnett's multiple comparison test). On the other hand, teprenone (the all-trans form:the 5Z-mono-cis form=6:4 (weight ratio)) did not show a significant neuroprotective effect.

Figure 7:
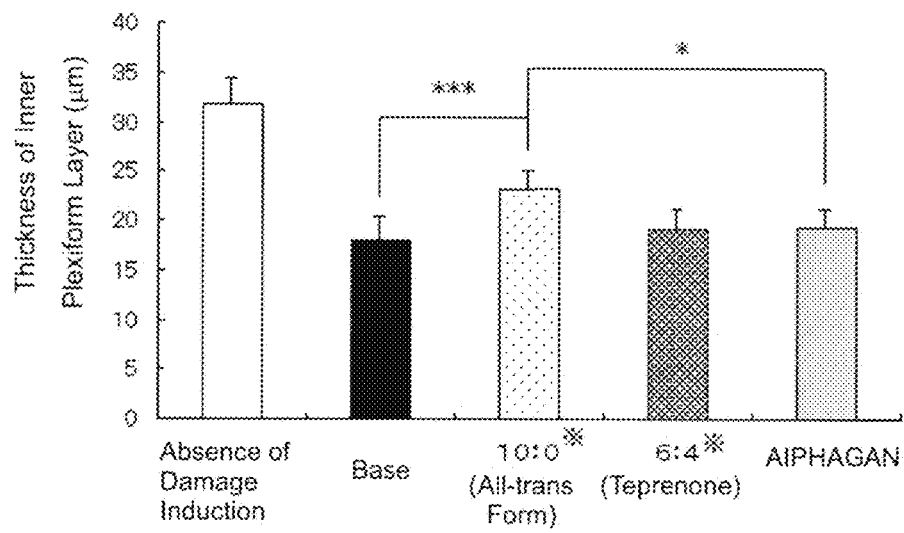
FIG. 7 shows the ocular neuroprotective action of the all-trans form in rat models with glaucoma induced by NMDA.

The results of Test Example 2 are shown in FIG. 7. As is apparent from FIG. 7, in the case of intravitreal administration, the all-trans form and the 5Z-mono-cis form showed significant neuroprotective effects against nerve damage by NMDA as compared with the base (***p<0.001, by Tukey-Kramer multiple comparison test). Even compared with AIPHAGAN (trade name) Ophthalmic Solution 0.1% (Senju Pharmaceutical), which is considered to have a neuroprotective effect, the all-trans form showed a significantly superior neuroprotective effect (*p<0.05, by Tukey-Kramer multiple comparison test).

Figure 8:
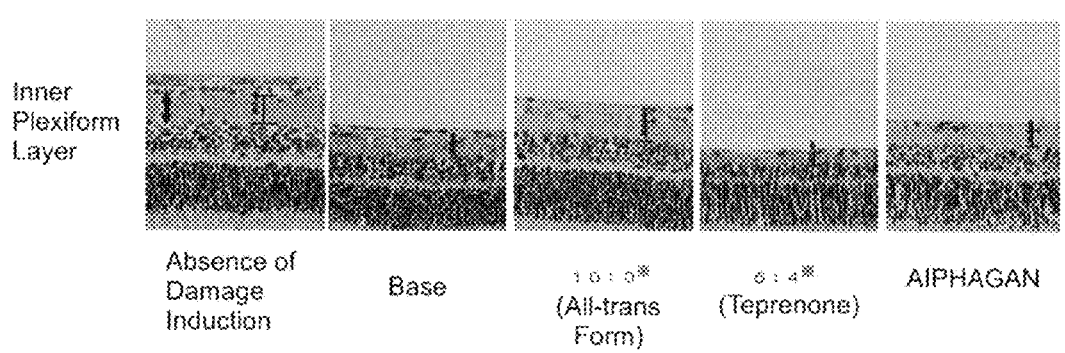
FIG. 8 shows increase in the thickness of the inner plexiform layer of the retina by the all-trans form in rat models with glaucoma induced by NMDA.

The photomicrographs of the histological sections of Test Example 2 are shown in FIG. 8.

Figure 9:
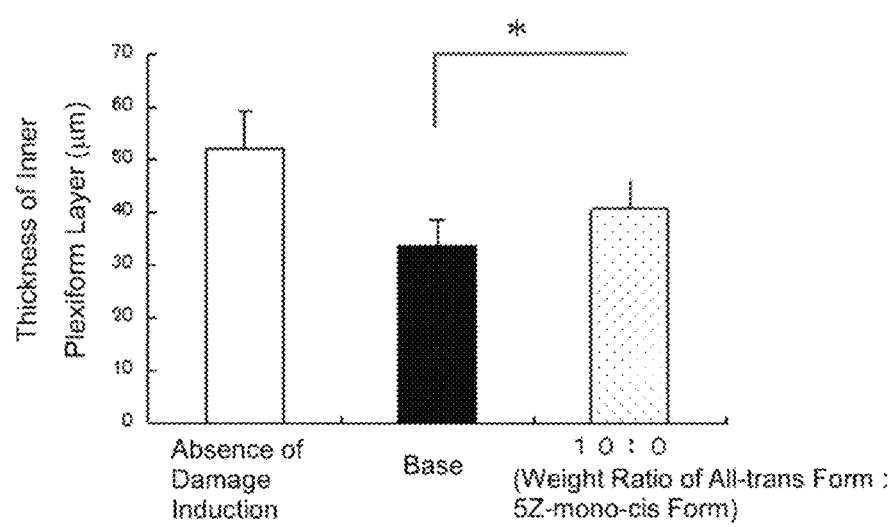
FIG. 9 shows the ocular neuroprotective action of the all-trans form in rat models with glaucoma induced by NMDA.

The results of Test Example 3 are shown in FIG. 9. As is apparent from FIG. 9, in the case of ocular instillation administration, the all-trans form showed a significant neuroprotective effect against nerve damage by NMDA as compared with the base (*p<0.05, by t-test).

(7) White Turbidity Reduction Test at Low Temperature Storage Preparation of Eye Drops Eye drops containing a marketed teprenone, GGA at different weight ratios (all-trans form: 5Z-mono-cis form=7:3, 8:2, 9:1, etc. (weight ratio)), or GGA consisting of the all-trans form purified by the above method were prepared as follows.

Specifically, to a surfactant (polysorbate 80) warmed to 65° C., the GGAs and GGA consisting of the all-trans form were separately added and dissolved under stirring in a hot water bath at 65° C. for 2 minutes. Water at 65° C. was added and each buffer was added under stirring to give a homogeneous solution. The pH and osmotic pressure were adjusted with hydrochloric acid and/or sodium hydroxide. This resulting solution was filtered through a membrane filter with a pore size of 0.2 μm (bottle top filter, Thermo Fisher Scientific) to give a clear sterile eye drop.

The constitutions of the eye drops are shown in Tables 3 to 8 below.

Before the preparation of the sterile eye drops, it was confirmed by HPLC described later that adsorption of GGA to instruments etc., which leads to the loss of the GGA content, did not occur during the preparation procedure.

Measurement Method for GGA Concentration

In accordance with the measurement conditions for the elution test described in PFSB/ELD Notification No. 0412007 "teprenone 100 mg/g fine granule", the GGA concentration of each eye drop was determined from the area value of the 5Z-mono-cis form (Ac) and the area value of the all-trans form (At) using Japanese pharmacopoeia "teprenone reference standard (all-trans form:5Z-mono-cis form=about 6:4 (weight ratio), Pharmaceutical and Medical Device Regulatory Science Society of Japan)" or teprenone (Wako Pure Chemical Industries) as a reference standard under the HPLC measurement conditions described below. For the eye drop containing teprenone (all-trans form: 5Z-mono-cis form=3:2 (weight ratio)), the GGA content was calculated by summing the amounts of the all-trans form and the 5Z-mono-cis form.

<HPLC Measurement Conditions>

Detector: ultraviolet absorption spectrometer (measurement wavelength: 210 nm)
Column: YMC-Pack ODS-A (inner diameter: 4.6 mm, length: 15 cm, particle diameter: 3 μm)
Column temperature: 30° C.
Mobile phase: 90% acetonitrile solution
Flow rate: 1.2 to 1.3 mL/min (the 5Z-mono-cis form and the all-trans form are eluted in this order.)
Injection volume: 5 μL of 0.05 g/100 mL sample
Storage at Low Temperature A 10 mL clear glass container (Nichiden-Rika Glass) was completely filled with each of the prepared eye drops (so that no air space remained). After sealing of the container, the eye drops were stored at 4° C. Immediately after the preparation and after stored at 4° C. for three days, 0.2 mL of each eye drop was transferred to wells of a 96-well plate (flat bottom, polystyrene) with a glass graduated pipette, and the absorbance was measured at 660 nm with a microplate reader (VersaMax, Molecular Devices) (temperature in the chamber: 20 to 25° C.). As referred to in JIS K0101 (Testing methods for industrial water, measurement of turbidity by light transmission), the absorbance at 660 nm of each sample was used as the indicator for white turbidity (the degree of turbidity).

The test procedure was carried out quickly. Before the test procedure was carried out, it was confirmed that the loss of the GGA content did not occur during the storage at 4° C. or the measurement of absorbance.

The degrees of turbidity were summarized with other data in Tables 3 to 6 below.

TABLE 3

| g/100 mL | Example 1 | Example 2 | Example 3 | Comparative Example 1 | Comparative Example 2 | Control (water) |
|---|---|---|---|---|---|---|
| All-trans form | 0.05 | — | — | — | — | — |
| All-trans form:5Z-mono-cis form weight ratio (9:1) | — | 0.05 | — | — | — | — |
| All-trans form:5Z-mono-cis form weight ratio (8:2) | — | — | 0.05 | — | — | — |
| All-trans form:5Z-mono-cis form weight ratio (7:3) | — | — | — | 0.05 | — | — |
| All-trans form:5Z-mono-cis form weight ratio (6:4) | — | — | — | — | 0.05 | — |
| Sodium dihydrogen phosphate dihydrate | 2.00 | 2.00 | 2.00 | 2.00 | 2.00 | — |
| Disodium hydrogen phosphate dodecahydrate | 0.40 | 0.40 | 0.40 | 0.40 | 0.40 | — |
| Polysorbate 80 | 0.25 | 0.25 | 0.25 | 0.25 | 0.25 | — |
| Hydrochloric acid | q.s. | q.s. | q.s. | q.s. | q.s. | — |
| Sodium hydroxide | q.s. | q.s. | q.s. | q.s. | q.s. | — |
| Purified water | q.s. | q.s. | q.s. | q.s. | q.s. | q.s. |
| pH | 5.7 | 5.7 | 5.7 | 5.7 | 5.7 | — |
| Osmotic pressure mOsm | 270 | 270 | 270 | 270 | 270 | — |
| Immediately after production 660 nm | 0.0358 | 0.0356 | 0.0377 | 0.0395 | 0.0401 | 0.0361 |
| 4° C. 3 days 660 nm | 0.0762 | 0.0922 | 0.1042 | 0.1137 | 0.1250 | 0.0353 |

TABLE 4

| g/100 mL | Example 4 | Example 5 | Example 6 | Comparative Example 3 | Comparative Example 4 | Control (water) |
|---|---|---|---|---|---|---|
| All-trans form | 0.05 | — | — | — | — | — |
| All-trans form:5Z-mono-cis form weight ratio (9:1) | — | 0.05 | — | — | — | — |
| All-trans form:5Z-mono-cis form weight ratio (8:2) | — | — | 0.05 | — | — | — |
| All-trans form:5Z-mono-cis form weight ratio (7:3) | — | — | — | 0.05 | — | — |
| All-trans form:5Z-mono-cis form weight ratio (6:4) | — | — | — | — | 0.05 | — |
| Sodium dihydrogen phosphate dihydrate | 1.40 | 1.40 | 1.40 | 1.40 | 1.40 | — |
| Disodium hydrogen phosphate dodecahydrate | 1.40 | 1.40 | 1.40 | 1.40 | 1.40 | — |
| Polysorbate 80 | 0.25 | 0.25 | 0.25 | 0.25 | 0.25 | — |
| Hydrochloric acid | q.s. | q.s. | q.s. | q.s. | q.s. | — |
| Sodium hydroxide | q.s. | q.s. | q.s. | q.s. | q.s. | — |
| Purified water | q.s. | q.s. | q.s. | q.s. | q.s. | q.s. |
| pH | 6.5 | 6.5 | 6.5 | 6.5 | 6.5 | — |
| Osmotic pressure mOsm | 260 | 260 | 260 | 260 | 260 | — |
| Immediately after production 660 nm | 0.0360 | 0.0357 | 0.0356 | 0.0401 | 0.0400 | 0.0361 |
| 4° C. 3 days 660 nm | 0.0734 | 0.0873 | 0.0993 | 0.1134 | 0.1164 | 0.0353 |

TABLE 5

| g/100 mL | Example 7 | Example 8 | Example 9 | Comparative Example 5 | Comparative Example 6 | Control (water) |
|---|---|---|---|---|---|---|
| All-trans form | 0.05 | — | — | — | — | — |
| All-trans form:5Z-mono-cis form weight ratio (9:1) | — | 0.05 | — | — | — | — |
| All-trans form:5Z-mono-cis form weight ratio (8:2) | — | — | 0.05 | — | — | — |
| All-trans form:5Z-mono-cis form weight ratio (7:3) | — | — | — | 0.05 | — | — |
| All-trans form:5Z-mono-cis form weight ratio (6:4) | — | — | — | — | 0.05 | — |
| Sodium dihydrogen phosphate dihydrate | 0.30 | 0.30 | 0.30 | 0.30 | 0.30 | — |
| Disodium hydrogen phosphate dodecahydrate | 3.20 | 3.20 | 3.20 | 3.20 | 3.20 | — |
| Polysorbate 80 | 0.25 | 0.25 | 0.25 | 0.25 | 0.25 | — |
| Hydrochloric acid | q.s. | q.s. | q.s. | q.s. | q.s. | — |
| Sodium hydroxide | q.s. | q.s. | q.s. | q.s. | q.s. | — |
| Purified water | q.s. | q.s. | q.s. | q.s. | q.s. | q.s. |
| pH | 7.5 | 7.5 | 7.5 | 7.5 | 7.5 | — |
| Osmotic pressure mOsm | 260 | 260 | 260 | 260 | 260 | — |
| Immediately after production 660 nm | 0.0358 | 0.0340 | 0.0374 | 0.0397 | 0.0366 | 0.0361 |
| 4° C. 3 days 660 nm | 0.0717 | 0.0837 | 0.0939 | 0.1065 | 0.1056 | 0.0353 |

TABLE 6

| g/100 mL | Example 10 | Example 11 | Example 12 | Comparative Example 7 | Comparative Example 8 | Control (water) |
|---|---|---|---|---|---|---|
| All-trans form | 0.05 | — | — | — | — | — |
| All-trans form:5Z-mono-cis form weight ratio (9:1) | — | 0.05 | — | — | — | — |
| All-trans form:5Z-mono-cis form weight ratio (8:2) | — | — | 0.05 | — | — | — |
| All-trans form:5Z-mono-cis form weight ratio (7:3) | — | — | — | 0.05 | — | — |
| All-trans form:5Z-mono-cis form weight ratio (6:4) | — | — | — | — | 0.05 | — |
| Boric acid | 1.30 | 1.30 | 1.30 | 1.30 | 1.30 | — |
| Borax | 0.40 | 0.40 | 0.40 | 0.40 | 0.40 | — |
| Polysorbate 80 | 0.25 | 0.25 | 0.25 | 0.25 | 0.25 | — |
| Hydrochloric acid | q.s. | q.s. | q.s. | q.s. | q.s. | — |
| Sodium hydroxide | q.s. | q.s. | q.s. | q.s. | q.s. | — |
| Purified water | q.s. | q.s. | q.s. | q.s. | q.s. | q.s. |
| pH | 7.5 | 7.5 | 7.5 | 7.5 | 7.5 | — |
| Osmotic pressure mOsm | 240 | 240 | 240 | 240 | 240 | — |
| Immediately after production 660 nm | 0.0352 | 0.0375 | 0.0372 | 0.0389 | 0.0394 | 0.0361 |
| 4° C. 3 days 660 nm | 0.1826 | 0.1919 | 0.1962 | 0.2373 | 0.2302 | 0.0353 |

The results in Tables 3 to 6 revealed that white turbidity after storage at 4° C. was significantly reduced in the eye drops containing the all-trans form in an amount of 80% by weight or more.

A 10 mL clear glass container (Nichiden-Rika Glass) was completely filled with each of the prepared eye drops (so that no air space remained). After sealing of the container, the eye drops were stored at 4° C. After stored at 4° C. for 6 days or 14 days, the absorbance was measured at 660 nm in the same manner as described above and used as the indicator for the degree of turbidity. Each sample was measured (n=4 or n=5) and comparison with control (water) was performed by Dunnett test.

Figure 10:
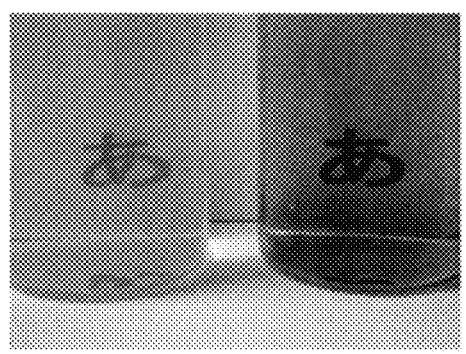
FIG. 10 shows the effect of reducing white turbidity during storage at low temperature, observed in a GGA-containing ophthalmic composition.

The measurement results of the degree of turbidity are shown with the results of the test in Table 7 below. The photograph of the eye drop stored at 4° C. for 14 days is shown in FIG. 10 (left: Comparative Example 10, right: Example 13).

TABLE 7

| g/100 mL | | Example 13 | Example 14 | Comparative Example 9 | Comparative Example 10 | Control (water) |
|---|---|---|---|---|---|---|
| All-trans form | | 0.05 | — | — | — | — |
| All-trans form:5Z-mono-cis form weight ratio (8:2) | | — | 0.05 | — | — | — |
| All-trans form:5Z-mono-cis form weight ratio (7:3) | | — | — | 0.05 | — | — |
| All-trans form:5Z-mono-cis form weight ratio (6:4) | | — | — | — | 0.05 | — |
| Sodium dihydrogen phosphate dihydrate | | 0.30 | 0.30 | 0.30 | 0.30 | — |
| Disodium hydrogen phosphate dodecahydrate | | 3.20 | 3.20 | 3.20 | 3.20 | — |
| Polysorbate 80 | | 0.35 | 0.35 | 0.35 | 0.35 | — |
| Hydrochloric acid | | q.s. | q.s. | q.s. | q.s. | — |
| Sodium hydroxide | | q.s. | q.s. | q.s. | q.s. | — |
| Purified water | | q.s. | q.s. | q.s. | q.s. | q.s. |
| pH | | 7.5 | 7.5 | 7.5 | 7.5 | — |
| Osmotic pressure mOsm | | 260 | 260 | 260 | 260 | — |
| 4° C. 6 days 660 nm | 1 | 0.0392 | 0.0383 | 0.0408 | 0.0395 | 0.0359 |
| | 2 | 0.0384 | 0.0394 | 0.0396 | 0.0396 | 0.0364 |
| | 3 | 0.0382 | 0.0386 | 0.0387 | 0.0405 | 0.0393 |
| | 4 | 0.0381 | 0.0383 | 0.0391 | 0.0396 | 0.0369 |
| | Mean | 0.0385 | 0.0387 | 0.0396 | 0.0398 | 0.0371 |
| | SD | 0.0005 | 0.0005 | 0.0009 | 0.0005 | 0.0015 |
| | P-value | 0.1368 | 0.0823 | 0.0048 | 0.0022 | — |
| 4° C. 14 days 660 nm | 1 | 0.0396 | — | — | 0.0644 | 0.0372 |
| | 2 | 0.0411 | — | — | 0.0693 | 0.0364 |
| | 3 | 0.0459 | — | — | 0.0734 | 0.0399 |
| | 4 | 0.0411 | — | — | 0.0683 | 0.0379 |
| | 5 | 0.0406 | — | — | 0.0695 | 0.0358 |
| | Mean | 0.0417 | — | — | 0.0690 | 0.0374 |

The results in Table 7 revealed that white turbidity after storage at 4° C. was significantly reduced in the eye drops containing the all-trans form in an amount of 80% by weight or more.

The results of Examples 7 to 12 are extracted from Tables 5 and 6 and shown in Table 8.

White turbidity after storage at low temperature was clearly reduced in the eye drops containing the phosphate buffering agents as compared with the eye drops containing the borate buffering agents.

TABLE 8

| g/100 mL | Example 7 | Example 8 | Example 9 | Example 10 | Example 11 | Example 12 |
|---|---|---|---|---|---|---|
| All-trans form | 0.05 | — | — | 0.05 | — | — |
| All-trans form:5Z-mono-cis form weight ratio (9:1) | — | 0.05 | — | — | 0.05 | — |
| All-trans form:5Z-mono-cis form weight ratio (8:2) | — | — | 0.05 | — | — | 0.05 |
| Sodium dihydrogen phosphate dihydrate | 0.30 | 0.30 | 0.30 | — | — | — |
| Disodium hydrogen phosphate dodecahydrate | 3.20 | 3.20 | 3.20 | — | — | — |
| Boric acid | — | — | — | 1.30 | 1.30 | 1.30 |
| Borax | — | — | — | 0.40 | 0.40 | 0.40 |
| Polysorbate 80 | 0.25 | 0.25 | 0.25 | 0.25 | 0.25 | 0.25 |
| Hydrochloric acid | q.s. | q.s. | q.s. | q.s. | q.s. | q.s. |
| Sodium hydroxide | q.s. | q.s. | q.s. | q.s. | q.s. | q.s. |
| Purified water | q.s. | q.s. | q.s. | q.s. | q.s. | q.s. |
| pH | 7.5 | 7.5 | 7.5 | 7.5 | 7.5 | 7.5 |
| Osmotic pressure mOsm | 260 | 260 | 260 | 240 | 240 | 240 |
| Immediately after production 660 nm | 0.0358 | 0.0340 | 0.0374 | 0.0352 | 0.0375 | 0.0372 |
| 4° C. 3 days 660 nm | 0.0717 | 0.0837 | 0.0939 | 0.1826 | 0.1919 | 0.1962 |

(8) White Turbidity Reduction Test at Normal Temperature Storage

The preparation of eye drops and the measurement of the GGA concentration were performed in the same manner as in "(7) White turbidity reduction test at low temperature storage" except that filtration in the preparation of the eye drops was not performed due to high concentration of GGA. The constitutions of the eye drops are shown in Table 9.

A 10 mL clear glass container (Nichiden-Rika Glass) was completely filled with the prepared eye drops (so that no air space remained). After sealing of the container, the eye drops were stored at room temperature (about 25° C.). After stored for three days, 0.2 mL of each of the eye drops was transferred to wells of a 96-well plate (flat bottom, polystyrene) with a glass graduated pipette, and the absorbance was measured at 660 nm with a microplate reader (VersaMax, Molecular Devices) (temperature in the chamber: 20 to 25° C.). As referred to in JIS K0101 (Testing methods for industrial water, measurement of turbidity by light transmission), the absorbance at 660 nm of each sample was used as the indicator for white turbidity (the degree of turbidity).

Each sample was measured (n=4) and comparison was performed by t-test between Comparative Example 11 and Example 13 and between Comparative Example 12 and Example 14. The results are shown in Table 9.

TABLE 9

| g/100 mL | | Example 13 | Comparative Example 11 | Example 14 | Comparative Example 12 | Water |
|---|---|---|---|---|---|---|
| All-trans form | | 3.000 | — | 1.000 | — | — |
| All-trans form:5Z-mono-cis form weight ratio (6:4) | | — | 3.000 | — | 1.000 | — |
| Sodium dihydrogen phosphate dihydrate | | 1.300 | 1.300 | 1.300 | 1.300 | — |
| Disodium hydrogen phosphate dodecahydrate | | 0.400 | 0.400 | 0.400 | 0.400 | — |
| POE castor oil | | 0.300 | 0.300 | 0.100 | 0.100 | — |
| POE hydrogenated castor oil 60 | | 6.000 | 6.000 | 2.000 | 2.000 | — |
| Polysorbate 80 | | 6.000 | 6.000 | 2.000 | 2.000 | — |
| Hydrochloric acid | | q.s. | q.s. | q.s. | q.s. | — |
| Sodium hydroxide | | q.s. | q.s. | q.s. | q.s. | — |
| Purified water | | q.s. | q.s. | q.s. | q.s. | q.s. |
| pH | | 7.64 | 7.61 | 7.59 | 7.55 | — |
| Osmotic pressure mOsm | | 307 | 314 | 255 | 253 | — |
| Room temperature 3 days 660 nm | 1 | 0.3521 | 0.7947 | 0.1786 | 0.3431 | 0.0372 |
| | 2 | 0.3631 | 0.8349 | 0.1800 | 0.3561 | 0.0368 |
| | 3 | 0.3633 | 0.7953 | 0.1805 | 0.3510 | 0.0373 |
| | 4 | 0.3591 | 0.7979 | 0.1914 | 0.3399 | 0.0379 |
| | Mean | 0.3594 | 0.8057 | 0.1826 | 0.3475 | 0.0373 |
| | P-value | ≤0.001 | | ≤0.001 | | — |

As is apparent from Table 9, white turbidity was significantly reduced in the eye drop containing relatively high concentration of the all-trans form as compared with the eye drop containing teprenone (the all-trans form:the 5Z-mono-cis form=6:4 (weight ratio)).

(9) Sensory Analysis

To a surfactant (polysorbate 80, POE castor oil) warmed to 65° C., teprenone and the all-trans form were separately added and dissolved under stirring in a hot water bath at 65° C. for 2 minutes. Water at 65° C. was added and each buffer was added under stirring to give a homogeneous solution. The pH and osmotic pressure were adjusted with hydrochloric acid and/or sodium hydroxide. This resulting solution was filtered through a membrane filter with a pore size of 0.2 µm (bottle top filter, Thermo Fisher Scientific) to give a clear sterile eye drop. The constitutions of the eye drops are shown in Table 10 below. Each of the eye drops was filled into a polyethylene terephthalate container (8 mL) in an aseptic manner.

About 30 µL of these eye drops were instilled into the eyes of non-contact lens-wearing nine healthy volunteers who were sensitive to irritating feeling (aged 33.8☐±6.6, eight male and one female) and the degrees of the "sting" in the eyes felt immediately after and 3 minutes after the instillation were evaluated by the VAS method (Visual Analogue Scale: visual assessment scale) (double blind study).

The results are shown in Table 10.

TABLE 10

| g/100 mL | Example 17 | Comparative Example 13 |
|---|---|---|
| All-trans form | 0.05 | — |
| All-trans form:5Z-mono-cis form weight ratio (6:4) | — | 0.05 |
| Boric acid | 1.30 | 1.30 |
| Borax | 0.40 | 0.40 |
| POE castor oil | 0.02 | 0.02 |
| Polysorbate 80 | 0.50 | 0.50 |
| Hydrochloric acid | q.s. | q.s. |
| Sodium hydroxide | q.s. | q.s. |

TABLE 10-continued

| g/100 mL | Example 17 | Comparative Example 13 |
|---|---|---|
| Purified water | q.s. | q.s. |
| pH | 7.5 | 7.5 |
| Osmotic pressure mOsm | 240 | 240 |
| Immediately after instillation VAS mean (%) | 19.3 | 37.3 |
| 3 minutes after instillation VAS mean (%) | 19.7 | 31.7 |

The results in Table 10 revealed that when the eye drop prepared with the all-trans form was used, "sting" in the eyes immediately after and 3 minutes after the instillation was significantly reduced, as compared with when the eye drop prepared with teprenone was used.

(10) Thermal Stability Test

To a surfactant (polysorbate 80, POE castor oil) warmed to 65° C., the all-trans form was added and dissolved under stirring in a hot water bath at 65° C. for 2 minutes. Water at 65° C. was added and each buffer was added under stirring to give a homogeneous solution. The pH and osmotic pressure were adjusted with hydrochloric acid and/or sodium hydroxide. This resulting solution was filtered through a membrane filter with a pore size of 0.2 μm (bottle top filter, Thermo Fisher Scientific) to give a clear sterile eye drop. The constitutions of the eye drops are shown in Table 11 below. A polyethylene terephthalate container (8 mL) (the container for Rohto Dryaid EX, Rohto Pharmaceutical) was completely filled with each of the eye drops in an aseptic manner.

For these eye drops, the stability test was performed by leaving them to stand in the upright position at 40° C., 50° C., or 60° C. for 10 days or 20 days. The all-trans form content in each sample was quantified using Japanese pharmacopoeia "teprenone reference standard (all-trans form: 5Z-mono-cis form=about 6:4 (weight ratio), Pharmaceutical and Medical Device Regulatory Science Society of Japan)" as a reference standard, and the residual ratio (%) was calculated. The total amount of the all-trans form and the mono-cis form in the reference standard were calculated as the GGA content.

Residual ratio(%)=100×[all-trans form content after being left to stand for predetermined period of time(g/100 mL)/all-trans form content immediately after production(g/100 mL)]

The results are shown in Table 11.

TABLE 11

| g/100 mL | | Example 18 | Example 19 | Example 20 | Example 21 |
|---|---|---|---|---|---|
| All-trans form | | 0.05 | 0.05 | 0.05 | 0.05 |
| Sodium dihydrogen phosphate dihydrate | | 2.00 | 1.40 | 0.30 | — |
| Disodium hydrogen phosphate dodecahydrate | | 0.40 | 1.40 | 3.20 | — |
| Boric acid | | — | — | — | 1.30 |
| Borax | | — | — | — | 0.40 |
| POE castor oil | | 0.02 | 0.02 | 0.02 | 0.02 |
| Polysorbate 80 | | 0.50 | 0.50 | 0.50 | 0.50 |
| Hydrochloric acid | | q.s. | q.s. | q.s. | q.s. |
| Sodium hydroxide | | q.s. | q.s. | q.s. | q.s. |
| Purified water | | q.s. | q.s. | q.s. | q.s. |
| pH | | 5.7 | 6.5 | 7.5 | 7.5 |
| Osmotic pressure mOsm | | 270 | 260 | 260 | 240 |
| Residual ratio (%) | 40° C. 20 days | 98.4 | 98.0 | 99.5 | 96.7 |
| | 50° C. 20 days | 91.9 | 94.3 | 99.6 | 72.4 |
| | 60° C. 10 days | 84.8 | 90.7 | 97.2 | 72.5 |
| | 60° C. 20 days | 67.3 | 81.1 | 91.2 | 48.5 |

The eye drops containing the phosphate buffering agents showed clearly higher residual ratios of the all-trans form and thus more excellent in the thermal stability, as compared with the eye drop containing the borate buffering agents. In terms of the pH range of 5.7 to 7.5, the eye drops having higher pH values showed higher residual ratios of the all-trans form and thus more excellent in the thermal stability.

(11) Light Stability Test

To a surfactant (polysorbate 80, POE castor oil) warmed to 65° C., the all-trans form was added and dissolved under stirring in a hot water bath at 65° C. for 2 minutes. Water at 65° C. was added and each buffer was added under stirring to give a homogeneous solution. The pH and osmotic pressure were adjusted with hydrochloric acid and/or sodium hydroxide. This resulting solution was filtered through a membrane filter with a pore size of 0.2 μm (bottle top filter, Thermo Fisher Scientific) to give a clear sterile eye drop. The constitutions of the eye drops are shown in Table 12 below. A polyethylene terephthalate container (8 mL) (the container for Rohto Dryaid EX, Rohto Pharmaceutical) was completely filled with each of the eye drops in an aseptic manner.

Each eye drop was subjected to light irradiation under the following conditions. The all-trans form content in each sample was quantified immediately after the production and after the irradiation and the residual ratio (%) was calculated.

Irradiation equipment: LTL-200A-15WCD (Nagano Science)
Light source: D-65 lamp
Total irradiation, temperature and humidity: 1,300,000 lx·h (4000 lx×325 hours), 25° C., 60% RH
Direction of light irradiation: the light was irradiated from the top to the container left to stand in the upright position on the spinning disk of the equipment.

Residual ratio(%)=100×[all-trans form content after light irradiation(g/100 mL)/all-trans form content immediately after production(g/100 mL)]

The results are shown in Table 12.

TABLE 12

| g/100 mL | Example 22 | Example 23 | Example 24 | Example 25 |
|---|---|---|---|---|
| All-trans form | 0.005 | 0.05 | 0.005 | 0.05 |
| Sodium dihydrogen phosphate dihydrate | 0.30 | 0.30 | — | — |
| Disodium hydrogen phosphate dodecahydrate | 3.20 | 3.20 | — | — |
| Boric acid | — | — | 1.30 | 1.30 |
| Borax | — | — | 0.40 | 0.40 |
| POE castor oil | 0.002 | 0.02 | 0.002 | 0.02 |
| Polysorbate 80 | 0.050 | 0.50 | 0.050 | 0.50 |
| Hydrochloric acid | q.s. | q.s. | q.s. | q.s. |
| Sodium hydroxide | q.s. | q.s. | q.s. | q.s. |
| Purified water | q.s. | q.s. | q.s. | q.s. |
| pH | 7.5 | 7.5 | 7.5 | 7.5 |
| Osmotic pressure mOsm | 260 | 260 | 240 | 240 |
| Residual ratio (%) | 90.5 | 92.8 | 86.1 | 89.0 |

The eye drops containing the phosphate buffering agents showed clearly higher residual ratios of the all-trans form and thus more excellent in the light stability, as compared with the eye drops containing the borate buffering agents.

(12) Test for Reduction in Adsorption to Contact Lenses

To a surfactant (polysorbate 80) warmed to 65° C., the all-trans form or a mixture of the all-trans form and the 5Z-mono-cis form (weight ratio=8:2) were separately added and dissolved under stirring in a hot water bath at 65° C. for 2 minutes. Water at 65° C. was added and each buffer was added under stirring to give a homogeneous solution. The pH and osmotic pressure were adjusted with hydrochloric acid and/or sodium hydroxide. This resulting solution was filtered through a membrane filter with a pore size of 0.2 μm (bottle top filter, Thermo Fisher Scientific) to give a clear sterile eye drop. The constitutions of the eye drops are shown in Table 13 below. A 4 mL clear glass container (Nichiden-Rika Glass) was completely filled with each eye drop.

One soft contact lens (hereinafter SCL: ACUVUE OASIS (Johnson & Johnson, approval number: 21800BZY10252000, base curve: 8.4 mm, diameter: 14.0 mm, power: −3.00 D) was immersed in 4 mL of each eye drop (immersion solution) and left to stand in the upright position at 25° C. for 14 hours. Each SCL had been initialized before use through immersion in 10 mL of physiological saline (Otsuka Normal Saline) overnight after being taken out from the package solution.

For 4 mL of the eye drop without immersion of SCL (blank solution), the same procedure as those for the eye drops with immersion of SCL (immersion solution) was performed. The amount of the all-trans form or the amount of the mixture of the all-trans form and the 5Z-mono-cis form was quantified by HPLC for each of the blank solution and the immersion solution, and the difference in the amounts between the blank solution and the immersion solution was used to calculate the amount of adsorption to SCL (μg/lens) (n=2).

Amount of adsorption(μg/lens)=[(amount of all-trans form or amount of mixture of all-trans form and 5Z-mono-cis form (weight ratio=8:2)in blank solution(g/100 mL)−amount of all-trans form or amount of mixture of all-trans form and 5Z-mono-cis form(weight ratio=8:2)in immersion solution (g/100 mL))/100]×4×1000×1000

The results are shown in Table 13.

TABLE 13

| g/100 mL | Example 26 | Example 27 | Example 28 | Example 29 | Example 30 | Example 31 |
|---|---|---|---|---|---|---|
| All-trans form | 0.05 | — | 0.05 | — | 0.05 | — |
| All-trans form:5Z-mono-cis form weight ratio (8:2) | — | 0.05 | — | 0.05 | — | 0.05 |
| Sodium dihydrogen phosphate dihydrate | 2.00 | 2.00 | 0.30 | 0.30 | — | — |
| Disodium hydrogen phosphate dodecahydrate | 0.40 | 0.40 | 3.20 | 3.20 | — | — |
| Boric acid | — | — | — | — | 1.30 | 1.30 |
| Borax | — | — | — | — | 0.40 | 0.40 |
| Polysorbate 80 | 0.25 | 0.25 | 0.25 | 0.25 | 0.25 | 0.25 |
| Hydrochloric acid | q.s. | q.s. | q.s. | q.s. | q.s. | q.s. |
| Sodium hydroxide | q.s. | q.s. | q.s. | q.s. | q.s. | q.s. |
| Purified water | q.s. | q.s. | q.s. | q.s. | q.s. | q.s. |
| pH | 5.7 | 5.7 | 7.5 | 7.5 | 7.5 | 7.5 |
| Osmotic pressure mOsm | 270 | 270 | 260 | 260 | 240 | 240 |
| Amount of adsorption (μg/lens) | 152.8 132.8 | 165.5 151.3 | 146.4 156.3 | 148.0 134.4 | 222.4 219.7 | 183.4 180.7 |

The eye drops containing the phosphate buffering agents showed clearly reduced adsorption of GGA to contact lenses, as compared with the eye drops containing the borate buffering agents.

INDUSTRIAL APPLICABILITY

The agent of the present invention is excellent in the prophylactic, ameliorating or therapeutic effect for a retinal disease and is also excellent as a preparation having advantages such that white turbidity after low temperature is reduced, etc.

The invention claimed is:

1. A method for ameliorating or treating a retinal disease selected from the group consisting of retinitis pigmentosa and age-related macular degeneration,
   the method comprising a step of bringing an effective amount of a composition comprising geranylgeranylacetone into contact with retinal pigment epithelial cells of a patient with the retinal disease, wherein the geranylgeranylacetone is selected from the group consisting of:
   (a) a mixture of at least two geometric isomers of geranylgeranylacetone, wherein the mixture contains at least 80% by weight or more of (5E,9E,13E)-geranylgeranylacetone relative to the total weight of the mixture, and
   (b) (5E,9E,13E)-geranylgeranylacetone,
   thereby ameliorating or treating the retinal disease,
      wherein the composition comprises a content of geranylgeranylacetone of 0.1 to 10% by weight when the composition is an ophthalmic composition in the form of a liquid, a fluid, a gel, or a semi-solid, and
      wherein a daily dose of the geranylgeranylacetone is 5 to 5000 mg when the composition is an oral agent.

2. The method according to claim 1, wherein (a) the mixture of at least two geometric isomers of geranylgeranylacetone is a mixture of (5E,9E,13E)-geranylgeranylacetone and at least one isomer selected from the group consisting of (5Z,9E,13E)-geranylgeranylacetone, (5E,9Z,13E)-geranylgeranylacetone and (5E,9E,13Z)-geranylgeranylacetone.

3. The method according to claim 1, wherein the composition is an ophthalmic composition, and bringing the effective amount of the composition in contact with the retinal pigment epithelial cells comprises contacting the ophthalmic composition comprising the geranylgeranylacetone to an eye of the patient with the retinal disease.

4. The method according to claim 1, wherein the composition is an oral agent, and bringing the effective amount of the composition in contact with the retinal pigment epithelial cells comprises an oral administration of the oral agent comprising the geranylgeranylacetone to the patient with the retinal disease.

5. The method according to claim 1, wherein bringing the effective amount of the composition in contact with the retinal pigment epithelial cells comprises an injection.

6. The method according to claim 1, wherein the composition further comprises at least one compound selected from the group consisting of a pharmaceutically acceptable base, a pharmaceutically acceptable carrier, an additive, a physiologically active ingredient other than geranylgeranylacetone and a pharmaceutically active ingredient other than geranylgeranylacetone.

7. A method for promoting the survival of retinal pigment epithelial cells,
the method comprising a step of bringing an effective amount of a composition comprising geranylgeranylacetone into contact with retinal pigment epithelial cells of a patient with a retinal disease selected from the group consisting of retinitis pigmentosa and age-related macular degeneration,
wherein the geranylgeranylacetone is selected from the group consisting of:
(a) a mixture of at least two geometric isomers of geranylgeranylacetone, wherein the mixture contains at least 80% by weight or more of (5E,9E,13E)-geranylgeranylacetone relative to the total weight of the mixture, and
(b) (5E,9E,13E)-geranylgeranylacetone,
thereby promoting the survival of the retinal pigment epithelial cells,
wherein the composition comprises a content of geranylgeranylacetone of 0.1 to 10% by weight when the composition is an ophthalmic composition in the form of a liquid, a fluid, a gel, or a semi-solid, and
wherein a daily dose of the geranylgeranylacetone is 5 to 5000 mg when the composition is an oral agent.

8. A method for suppressing retina inflammation,
the method comprising a step of bringing an effective amount of a composition comprising geranylgeranylacetone into contact with retinal pigment epithelial cells of a patient with a retinal disease selected from the group consisting of retinitis pigmentosa and age-related macular degeneration, wherein the geranylgeranylacetone is selected from the group consisting of:
(a) a mixture of at least two geometric isomers of geranylgeranylacetone, wherein the mixture contains at least 80% by weight or more of (5E,9E,13E)-geranylgeranylacetone relative to the total weight of the mixture, and
(b) (5E,9E,13E)-geranylgeranylacetone,
thereby suppressing retina inflammation,
wherein the composition comprises a content of geranylgeranylacetone of 0.1 to 10% by weight when the composition is an ophthalmic composition in the form of a liquid, a fluid, a gel, or a semi-solid, and
wherein a daily dose of the geranylgeranylacetone is 5 to 5000 mg when the composition is an oral agent.

9. The method according to claim 1, wherein the composition is an ophthalmic composition and the composition is administered so that a daily dose of the geranylgeranylacetone is 50 ng to 50 mg.

10. The method according to claim 3, wherein the ophthalmic composition is an eye drop, and wherein the eye drop is administered 1 to 5 times per day in an amount of 1 to 2 drops each time.

11. A method for ameliorating or treating a retinal disease selected from the group consisting of retinitis pigmentosa and age-related macular degeneration while suppressing eye irritancy,
the method comprising a step of bringing an effective amount of an ophthalmic composition comprising geranylgeranylacetone into contact with retinal pigment epithelial cells of a patient with the retinal disease, wherein the geranylgeranylacetone is selected from the group consisting of:
(a) a mixture of at least two geometric isomers of geranylgeranylacetone, wherein the mixture contains at least 80% by weight or more of (5E,9E,13E)-geranylgeranylacetone relative to the total weight of the mixture, and
(b) (5E,9E,13E)-geranylgeranylacetone,
thereby ameliorating or treating the retinal disease involving the impairment of retinal pigment epithelial cells while suppressing eye irritancy,
wherein the composition comprises a content of geranylgeranylacetone of 0.1 to 10% by weight when the composition is an ophthalmic composition in the form of a liquid, a fluid, a gel, or a semi-solid, and
wherein a daily dose of the geranylgeranylacetone is 5 to 5000 mg when the composition is an oral agent.

12. A method for suppressing the degeneration, impairment or destruction of retinal pigment epithelial cells,
the method comprising a step of bringing an effective amount of an ophthalmic composition comprising geranylgeranylacetone into contact with retinal pigment epithelial cells of a patient with a retinal disease selected from the group consisting of retinitis pigmentosa and age-related macular degeneration, wherein the geranylgeranylacetone is selected form the group consisting of:
(a) a mixture of at least two geometric isomers of geranylgeranylacetone, wherein the mixture contains at least 80% by weight or more of (5E,9E,13E)-geranylgeranylacetone relative to the total weight of the mixture, and
(b) (5E,9E,13E)-geranylgeranylacetone,
thereby suppressing the degeneration, impairment or destruction of retinal pigment epithelial cells,
wherein the composition comprises a content of geranylgeranylacetone of 0.1 to 10% by weight when the composition is an ophthalmic composition in the form of a liquid, a fluid, a gel, or a semi-solid, and
wherein a daily dose of the geranylgeranylacetone is 5 to 5000 mg when the composition is an oral agent.

13. A method for suppressing retina inflammation,
the method comprising a step of bringing an effective amount of a composition comprising (5Z,9E,13E)-geranylgeranylacetone into contact with retinal pigment epithelial cells of a patient with a retinal disease selected from the group consisting of retinitis pigmentosa and age-related macular degeneration, and thereby suppressing retina inflammation,
wherein the composition comprises a content of geranylgeranylacetone of 0.1 to 10% by weight when the composition is an ophthalmic composition in the form of a liquid, a fluid, a gel, or a semi-solid, and
wherein a daily dose of the geranylgeranylacetone is 5 to 5000 mg when the composition is an oral agent.

* * * * *